(12) United States Patent  
Imura

(10) Patent No.: US 7,262,854 B2  
(45) Date of Patent: Aug. 28, 2007

(54) MULTI-ANGLE COLORIMETER

(75) Inventor: Kenji Imura, Toyohashi (JP)

(73) Assignee: Konica Minolta Sensing, Inc., Osaka (JP)

( * ) Notice: Subject to any disclaimer, the term of this patent is extended or adjusted under 35 U.S.C. 154(b) by 71 days.

(21) Appl. No.: 11/159,666

(22) Filed: Jun. 23, 2005

(65) Prior Publication Data

US 2005/0286053 A1    Dec. 29, 2005

(30) Foreign Application Priority Data

Jun. 25, 2004   (JP)   ............................. 2004-188147

(51) Int. Cl.  
*G01J 3/46* (2006.01)

(52) U.S. Cl. ...................................... 356/402; 356/405

(58) Field of Classification Search ................. 356/402  
See application file for complete search history.

(56) References Cited

U.S. PATENT DOCUMENTS 6,707,553 B1 *   3/2004   Imura ......................... 356/402

\* cited by examiner

*Primary Examiner*—Roy M. Punnoose  
(74) *Attorney, Agent, or Firm*—Brinks Hofer Gilson & Lione

(57) ABSTRACT

In a multi-angle colorimeter having an illumination system that illuminates a sample surface and a plurality of light receiving systems that receive reflected light therefrom, an illumination system for orientation error detection is provided that illuminates the sample surface from substantially close direction to the normal of the sample surface. Actual measured reflectance factor is corrected based on the specific approximation function obtained from the measured reflectance factor and detected orientation error.

15 Claims, 18 Drawing Sheets

ASPECULAR ANGLE

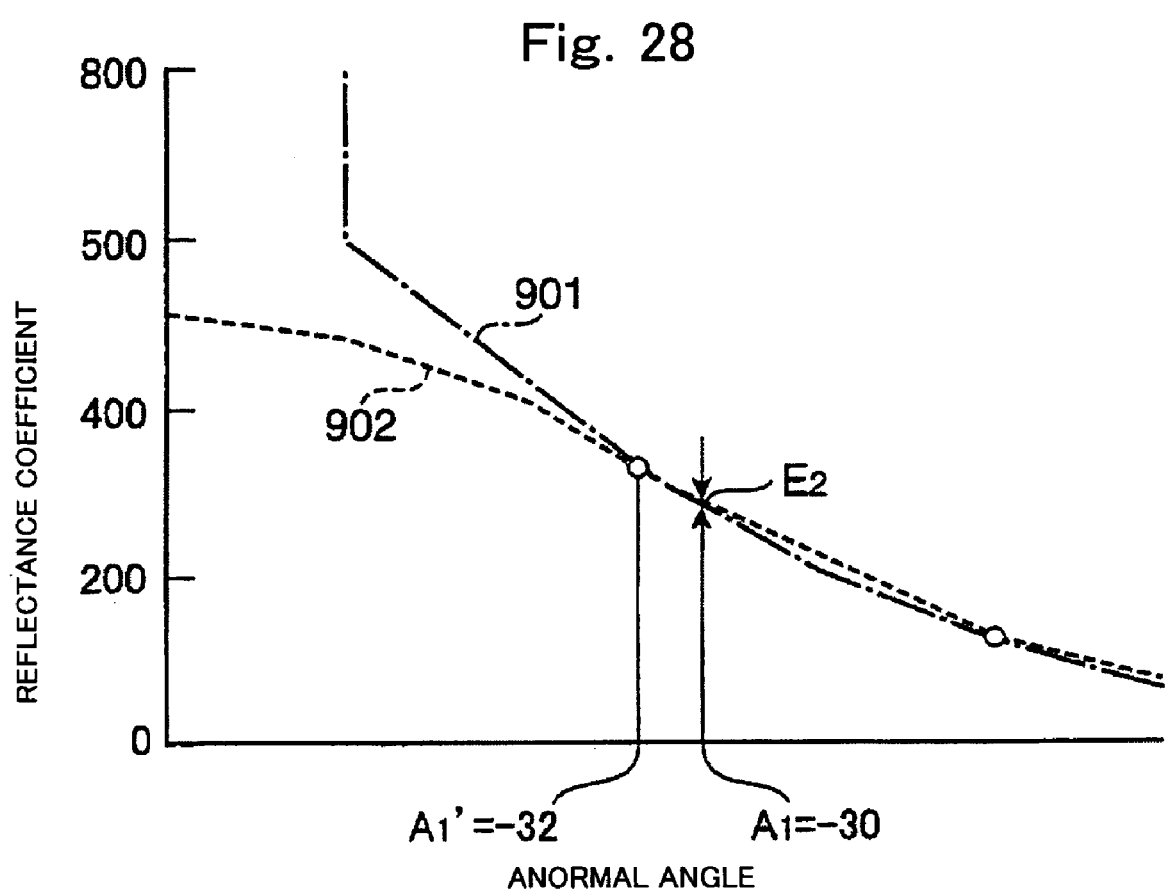

MULTI-ANGLE COLORIMETER

This application is based on the application No. 2004-188147 filed in Japan, the contents of which are hereby incorporated by reference.

BACKGROUND OF THE INVENTION

1. Field of the Invention

The present invention relates to a multi-angle colorimeter for measuring a gonio-apparent coating such as a metallic coating or a pearlescent coating, and more particularly, to a multi-angle colorimeter having a function for correcting the geometry errors.

2. Description of the Related Art

In metallic coatings and pearlescent coatings used primarily for an automotive coating, tiny flakes of aluminum or mica called special effect pigment are contained within the coating, and this produces a so-called metallic effect or pearlescent effect. This is due to the fact that the contribution of the special effect pigment to the reflection characteristic differs according to the illumination and the viewing direction. For the evaluation (calorimetric measurement) of such coatings, a multi-angle colorimeter that has a multi-angle geometry (optical system) is used. A multi-angle colorimeter having the multi-angle geometry illuminates from a plurality of directions and receives reflected light from a single direction or illuminates from a single direction and receives reflected light from a plurality of directions.

However, generally, the following two geometry errors are inevitable in the multi-angle colorimeter of prior arts:

(1) Initial directional error: This error is caused because the angles from the normal of the sample surface to be measured (anormal angles, hereafter) of the illumination and the receiving are deviated from the nominal angles due to various manufacturing errors.

(2) Orientation error: This error is caused by the disagreement between the normal of the sample surface and the reference axis of the measuring device both of which are to be in coincidence ideally. This error readily occurs when the sample surface is not a plane.

These geometry errors significantly affect the measurement stability particularly in the vicinity of the specular reflection direction where the directional dependence of the reflection characteristics is very high. For example, in a multi-angle colorimeter illuminating from a direction of 45 degrees in anormal angle and receives reflected light from five directions of 15 degrees, 25 degrees, 45 degrees, 75 degrees and 110 degrees in angles from the specular reflection direction (aspecular angles, hereafter), the influence of the geometry errors on measurement values is particularly large in directions of 15 degrees and 25 degrees in aspecular angle.

To reduce the influence of the orientation error, a correcting technique of the orientation error has been proposed. According to this method, the influence of the orientation error is estimated based on a mathematical function approximating the direction dependence of the reflection characteristic of the sample illuminated from the direction of 45 degrees in anormal angle, and then corrected based on the estimated error.

However, the above-described method doesn't correct the influence of the orientation error accurately since the illumination from the direction of 45 degrees anormally in typical multi-angle colorimeters is used as the illumination for detecting the orientation error. That is, the reflection characteristic is not symmetrical in both sides of the specular direction for the illumination from 45 degrees in anormal angle largely away from the normal of the sample surface because of the asymmetrical optical characteristics of the sample. For this reason, the approximation accuracy of the mathematical function is generally insufficient, and accordingly the accuracy of the orientation error estimated based on the approximation function is also insufficient.

SUMMARY OF THE INVENTION

A multi-angle colorimeter comprising: one or plural illuminators for illuminating a surface of an object to be measured from one or plural directions, and for measuring a calorimetric of the surface of the object; one or plural light receivers for receiving reflected light from the surface illuminated by said one or plural illuminators respectively, and for measuring a calorimetric of the surface of the object; a reflection characteristics calculator for calculating a reflectance characteristics of the surface for plural directions of illumination or light receiving; an angular error detector for detecting an angular error of the illuminators and the light receivers with respect to the surface, and comprising a measurement system different from the illuminators and the light receivers; an approximation function setter for determining an approximation function that approximates a directional dependence of the reflectance characteristics of the surface based on the detected angular error and the reflection characteristics obtained by said reflection characteristics calculator; a reflection characteristics error estimator for estimating an error of the reflection characteristics in each measurement direction based on the determined approximation function and the detected angular error; and a corrector for correcting the obtained reflection characteristics in each measurement direction based on the estimated reflection characteristics error.

In the following description, like parts are designated by like reference numbers throughout the several drawings.

BRIEF DESCRIPTION OF THE DRAWINGS

FIG. 28 is a graph showing the residual error of reflectance factors when the actual anormal angle A1' of a first light receiving system is −32 degrees and the nominal anormal angle A1 is −30 degrees.

DETAILED DESCRIPTION OF THE PREFERRED EMBODIMENT

Hereinafter, embodiments will be described with reference to the drawings.

First Embodiment

Correction of the Orientation Error

Figure 1A:
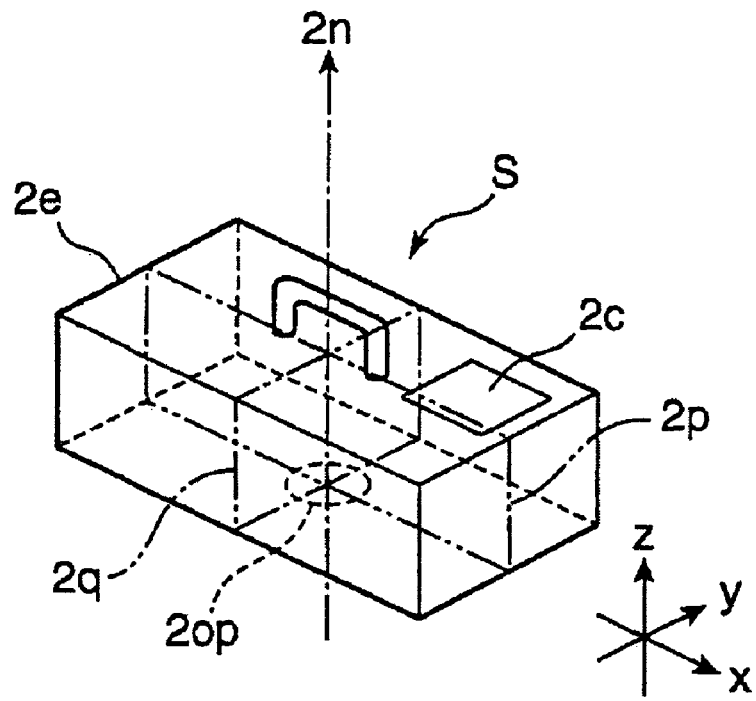
FIGS. 1(a) and 1(b) are views schematically showing a multi-angle colorimeter, FIG. 1(a) being a perspective view schematically showing the appearance of the multi-angle colorimeter, FIG. 1(b) being a cross-sectional view of a measurement aperture.

FIG. 1(a) is a perspective view schematically showing the appearance of a multi-angle colorimeter S. This multi-angle colorimeter S has a box-shaped body case 2e in which components such as an illumination system, a light receiving system or the like described later are housed. The bottom surface of the body case 2e is a measurement aperture surface 2. On the measurement aperture surface 2, a measurement aperture 2op of an appropriate shape (for example, an oval) is formed. In an appropriate position on the surface of the body case 2e, a display 2c for showing the measurement result and the like are disposed. The multi-angle colorimeter S is portable and handheld.

Figure 1B:
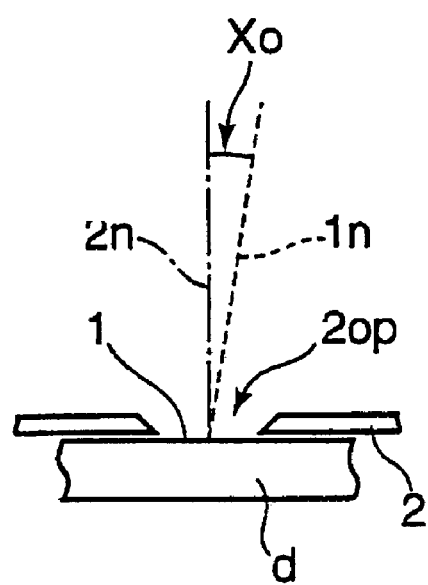

Then, the calorimetric measurement of the sample surface 1 (for controlling metallic colors for example) is performed with the measurement aperture 2op of the multi-angle colorimeter S being opposed to a sample surface 1 of a measurement sample d (the exterior surface of a car coated by a metallic or pearlescent coating for example; hereinafter, merely referred to "sample surface 1") as shown in FIG. 1(b). When the normal 1n of the sample surface 1 (hereinafter, referred to as "sample surface normal 1n") is tilted by $X_0$ with respect to the reference axis 2n of the multi-angle colorimeter S (generally the normal of the measurement aperture surface 2; hereinafter, referred to as "reference axis 2n"), the angle $X_0$ is the orientation error. That is, when the sample surface 1 is correctly placed on the measurement aperture surface 2, the reference axis 2n coincides with the sample surface normal 1n ($X_0=0$), so that measurement without any orientation error can be performed. However, in the actual measurement, it is difficult to realize $X_0=0$. In particular, when the sample surface 1 is curved, the difficulty increases. Therefore, according to the first embodiment, the error caused by the tilt angle $X_0$ is corrected.

Figure 2:
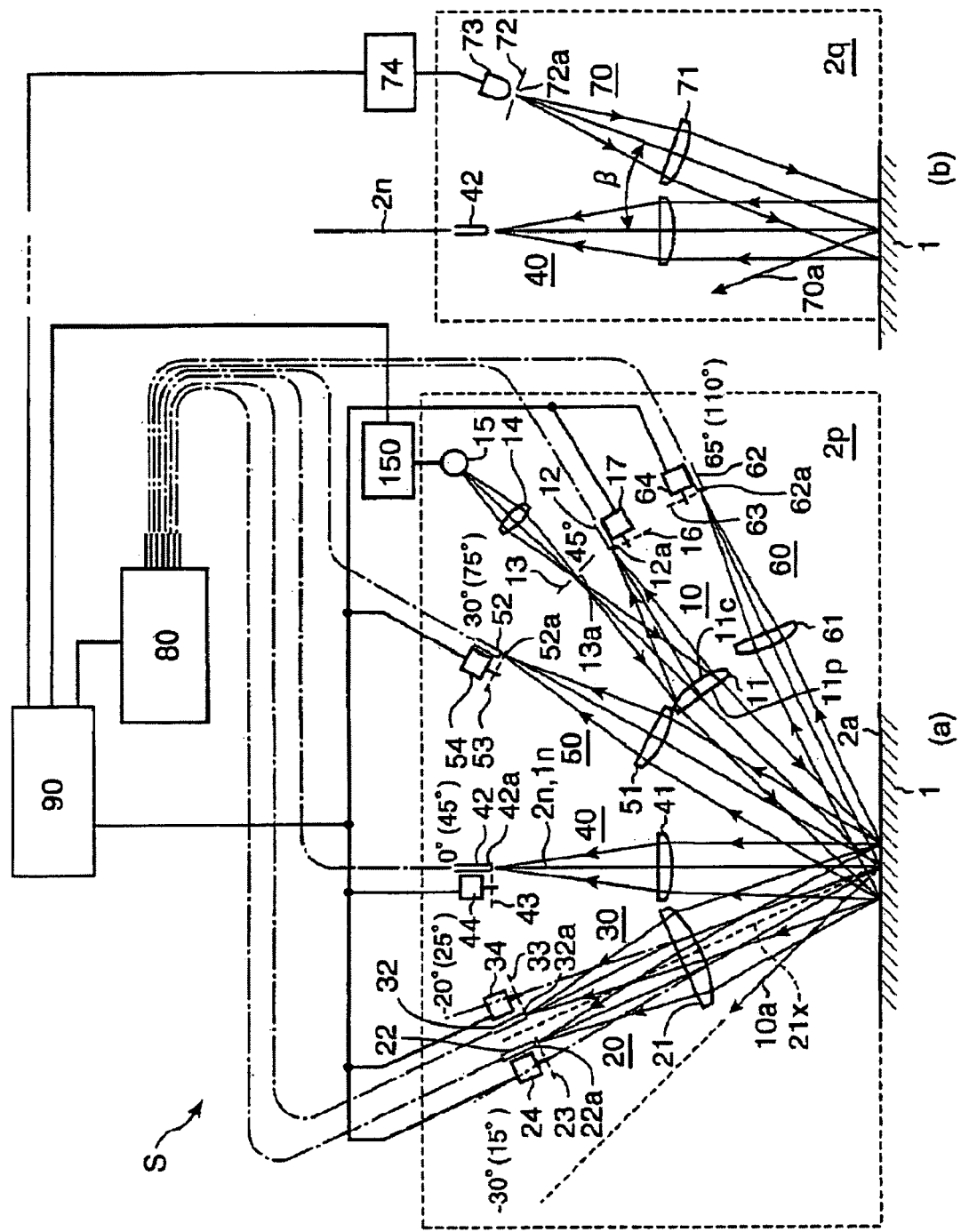
FIGS. 2(a) and 2(b) are cross-sectional views showing the internal structure of the multi-angle colorimeter S, FIG. 2(a) showing the arrangement of an illuminator and light receivers in a first measurement plane $2p$ containing the X-axis and the reference axis $2n$, FIG. 2(b) showing the arrangement of an illuminator and a light receiver in a second measurement plane $2q$ orthogonal to the measurement plane $2p$ containing the Y-axis and the reference axis $2n$.

FIGS. 2(a) and 2(b) are structural views showing the internal structure of the multi-angle colorimeter S as the first embodiment. FIG. 2(a) shows the arrangement of an illumination and light receiving system on a first measurement plane 2p that contains the reference axis 2n and the X-axis shown in FIG. 1(a). FIG. 2(b) shows the arrangement of an illumination and light receiving system on a second measurement plane 2q that contains the reference axis 2n and is orthogonal to the first measurement plane 2p.

In FIGS. 2(a) and 2(b), the multi-angle colorimeter S is provided with: an illumination system 10; a first to fifth light receiving systems 20 to 60; an illumination system for orientation error detection 70; a spectroscope 80 that separates the received reflected light according to the wavelength and generates spectral data corresponding to the light intensity in each wavelength; and an arithmetic control unit 90 that performs the control of the measurement, the computing for the angle error correction, and the like.

As shown in FIG. 2(a), the optical axes of the illumination system 10 and the first to fifth light receiving systems 20 to 60 are within the measurement plane 2p. The illumination system 10 illuminates the sample surface 1 from a direction of an angle $A_0$ (45 degrees) from the reference axis 2n. Among lights reflected from the sample surface 1, the lights reflected in directions of anormal angles Am (m=1 to 5) which are −30, −20, 0, 30 and 65 degrees are received by the light receiving systems 20, 30, 40, 50 and 60, respectively. Hereafter, with respect to the reference axis 2n, anormal angles on the same side as the illumination direction are positive, and those on the opposite side are negative.

The anormal angle Am is converted into an aspecular angle Bm which is an angle from a specular direction 10a for the illumination by the illumination system 10 by adding the anormal angle $A_0$, that is, Bm=Am+$A_0$. Therefore, in this case, anormal angles Am of −30, −20, 0, 30 and 65 degrees are converted into specular angles Bm of 15, 25, 45, 75 and 110 degrees (m=1 to 5), respectively. The parenthesized angles in FIG. 2(a) are the aspecular angles Bm. By thus arranging the first to fifth light receiving systems 20 to 60, the aspecular angles of 15, 45 and 110 degrees required by ASTM E2194 and the aspecular angles of 25, 45 and 75 degrees required by DIN6175-2, 2001 are included in the embodiment. As ASTM E2194 and DIN6175-2, 2001 are principal standards of the method for evaluating metallic and pearlescent coatings, the multi-angle colorimeter S is built suitably for the evaluating metallic and pearlescent coatings.

The multi-angle colorimeter S according to the present embodiment is further provided with the illumination system 70 for the orientation error detection as shown in FIG. 2(b). The illumination system 70 has the optical axis within the measurement plane 2q orthogonal to the measurement plane 2p, and is disposed so as to illuminate the sample surface 1 from a direction of a predetermined angle β from the reference axis 2n.

The illumination system 10 comprises: a light source 15 comprising a halogen lamp, a xenon lamp or the like; a source driving circuit 150 that drives the light source 15; a relay lens 14; a light source aperture plate 13 that restricts the light flux from the light source 15; a monitor optical fiber 12; and a collimator lens 11. The light flux emitted from the light source 15 converges at an aperture 13a of the light source aperture forming an image of the light source 15 by the relay lens 14. The light source aperture plate 13 is disposed so that the aperture 13a thereof positions at the focal position of the collimator lens 11. The luminous flux from the light source 15 having passed through the aperture 13a is collimated into a parallel flux by the collimator lens 11, and illuminates the sample surface 1 from the direction of the anormal angle of 45 degrees.

The collimator lens 11 as a plano-convex lens has its convex surface 11c oriented toward the light source 15, and the lens axis thereof is slightly tilted with respect to the optical axis of the illumination system. With this arrangement, substantially 5% of the light flux incident on the convex surface 11c and collimated into a parallel light flux is reflected at a plane surface 11p of the collimator lens 11, again converged at the convex surface 11c, and incident as monitor light on the incident end 12a of the monitor optical fiber 12 constituting a reference system. A shutter 16 is disposed immediately in front of the incident end 12a. The shutter 16 is actuated to either of open or close position by the driver 17 controlled by the arithmetic control unit 90. By controlling the position of the shutter 16, the incidence of the monitor light on the incident end 12a is controlled.

The illumination system 70 comprises: a light source 73 comprising a spot light source such as an LED; a source driving circuit 74 that drives the light source 73; a light source aperture plate 72 that restricts the light flux from the light source 73; and a collimator lens 71. The light source aperture plate 72 is disposed so that an aperture 72a thereof positions at the focal position of the collimator lens 71. The light flux from the light source 73 having passed through the aperture 72a of the light source aperture plate 72 is collimated into a parallel light flux by the collimator lens 71. The direction of illumination light by the illumination system 70 is close to the reference axis 2n (tilted by a small angle β from the reference axis 2n) within the measurement plane 2q orthogonal to the measurement plane 2p.

The first to fifth light receiving systems 20 to 60 comprise: collimator lenses 21, 41, 51 and 61 that converge the parallel light flux reflected by the sample surface 1; measurement optical fibers 22, 32, 42, 52 and 62 with incident ends 22a, 32a, 42a, 52a and 62a disposed at the focus positions of the collimator lenses 21, 41, 51 and 61; and a spectroscope 80 connected to the exit ends of the measurement optical fibers 22, 32, 42, 52 and 62.

The third, fourth and fifth light receiving systems 40, 50 and 60 (the anormal angles A3, A4 and A5 are 0 degree, 30 degrees and 65 degrees respectively) comprise the individual collimator lenses 41, 51 and 61 and measurement optical fibers 42, 52 and 62, respectively. Consequently, the reflected lights from the sample surface in the directions of the anormal angles of 0 degree, 30 degrees and 65 degrees are converged by the collimator lenses 41, 51 and 61 and incident on the incident ends 42a, 52a and 62a of the corresponding measurement optical fibers, and the incident light is transmitted to the spectroscope 80.

On the other hand, the first and second light receiving systems 20 and 30 (the anormal angles A1 and A2 are −30 degrees and −20 degrees respectively) comprise the common collimator lens 21 and their respective measurement optical fibers 22 and 32. The lens axis 21x of the collimator lens 21 is oriented to the bisector of anormal angles of −20 degrees and −30 degrees. The optical axes of the first and second light receiving system 20 and 30 comprising the common collimator lenses 21 and the incident ends 22a and 32a of the measurement optical fibers 22 and 32 are at the anormal angles of −20 degrees and −30 degrees respectively which are bisected by the lens axis 21x. Consequently, the reflected lights from the sample surface in the directions of the anormal angles of −20 degrees and −30 degrees are converged by the common collimator lenses 21 and incident on the incident ends 22a and 32a of the corresponding measurement optical fibers respectively. Since the angle between the first light receiving system 20 and the second light receiving system 30 is as small as 10 degrees, if a collimator lens is provided for each of the systems 20 and 30, it is necessary to increase the distance from the sample surface 1 and accordingly to increase the size of the illumination and light receiving system. However, by providing the common collimator lens 21 as described above, the distance from the sample surface 1 can be same as other receiving systems and a compact illumination and light receiving system can be attained.

Immediately in front of the incident ends 22a to 62a of the first to fifth light receiving systems 20 to 60, shutters 23, 33, 43, 53 and 63 are disposed. Each of the shutters 23, 33, 43, 53 and 63 is actuated to either of open or close position by driver 24, 34, 44, 54 or 64 respectively controlled by the arithmetic control unit 90. By controlling the position of the shutters 23, 33, 43, 53 and 63, the incidence of the reflected lights on the incident ends 22a to 62a is controlled.

Figure 3:
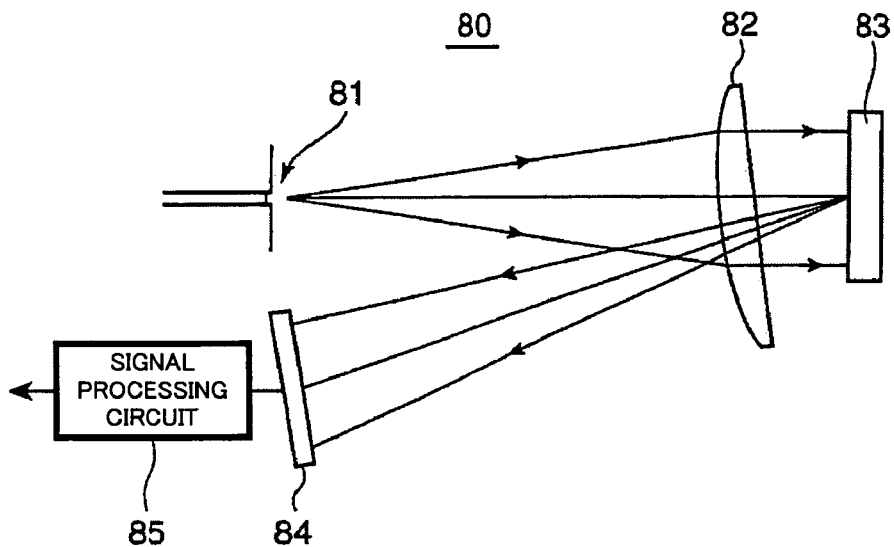
FIG. 3 schematically shows the structure of a spectroscope 80.

The spectroscope 80 separates the received light according to the wavelength and generates spectral data corresponding to the intensities of spectrally separated lights. As shown in FIG. 3, the spectroscope 80 comprises a polychromator 801 that simultaneously measures for all wavelengths in the measurement wavelength range and a signal processing circuit 85. The polychromator 801 comprises: an incident slit 81 served as the inlet of the received light to the spectroscope 80; an imaging lens 82 that generates a dispersed image of the incident slit 81; a diffraction grading 83; and a sensor array 84 disposed at the imaging position of the dispersed image of the incident slit.

Figure 4:
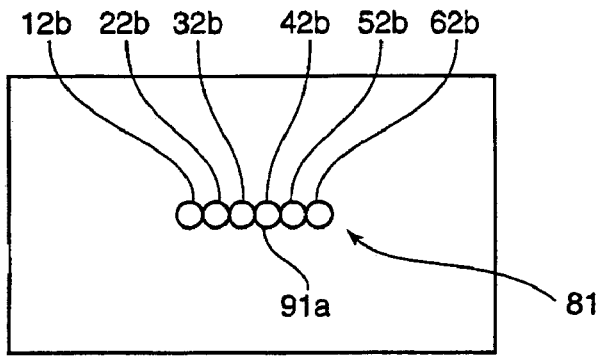
FIG. 4 shows an example of an incident slit 81 of the spectroscope 80.

The incident slit 81 is a rectangular slit provided on the housing or the like of the spectroscope 80 as shown in FIG. 4. In the incident slit 81, the exit ends 12b, 22b, 32b, 42b, 52b and 62b of the monitor optical fiber 12 and the measurement optical fibers 22, 32, 42, 52 and 62 are disposed in alignment. In the slit configuration shown in FIG. 4, the exit ends 12b, 22b, 32b, 42b, 52b and 62b are arranged in a single row. When single optical fibers with outer diameter of 0.5 mm are used as the monitor optical fiber 12 and the measurement optical fibers 22, 32, 42, 52 and 62 for example, the exit ends are arranged close to each other in the incident slit 81 of 0.5 mm width and 3 mm length.

The monitor light and the reflected lights incident on the incident ends 12a, 22a, 32a, 42a, 52a and 62a exit from the exit ends 12b, 22b, 32b, 42b, 52b and 62b disposed in alignment in the incident slit 81. These exit lights are directed to the sensor array 84 via the imaging lens 82 and the diffraction grading 83.

The sensor array 84 is, for example, a photo diode array of 40 pixels (pixel number n=1 to 40) the pixel size of which is 0.5 mm width and 3 mm length in accordance with the size of the incident slit 81. Therefore, the imaging lens 82 and the diffraction grating 83 generate the dispersed image of the dispersion length corresponding to the size of the sensor array 84 (20 mm and pixel dispersion is 10 nm/pixel in this case) by the light emitted from the six exit ends 12b, 22b, 32b, 42b, 52b or 62b.

Figure 5:
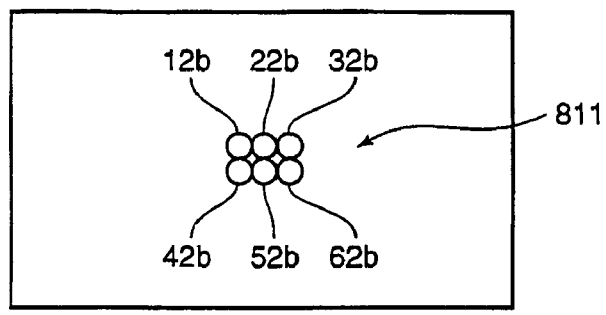
FIG. 5 shows another example of the incident slit 81 of the spectroscope 80.

Instead of the above-described incident slit 81 of single row arrangement, an incident slit 811 by double row arrangement as shown in FIG. 5 may be used. In the double row arrangement, an incident slit 811 is formed by exit ends 12b, 22b and 32b arranged in the first row and exit ends 42b, 52b and 62b arranged in the second row, stacked each other. In this case, with optical fibers of the same size as the case of FIG. 4, the incident slit 811 is a rectangular of 1 mm width and 1.5 mm length. When the incident slit 811 is used, the dispersed images of the lights exited from the exit ends 12b, 22b and 32b in the first row and 42b, 52b and 62b in the second row are imaged on adjoining pixels of the sensor array 84. By arranging exit ends in two rows, the slit length can be shorter than that of the single row arrangement, and as the result the influence of aberrations on the dispersed image can be reduced. Moreover, the cost can be reduced due to the reduced size of the sensor array.

Figure 6:
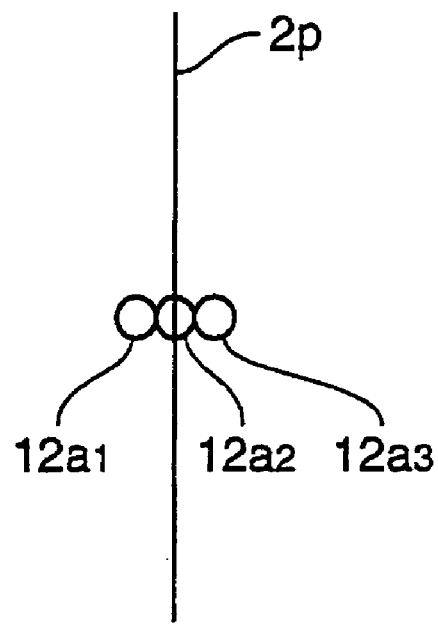
FIG. 6 shows an example of the structure of an incident end of a monitor optical fiber 12 in a reference system.

Since the angular error in a direction orthogonal to the measurement plane $2p$ does not significantly affect the reflection characteristic, a plurality of optical fibers can be used in each of the monitor system and the light receiving system instead of a single fiber to receive more quantity of light. For example, three monitor optical fibers can be used for the monitor system and the incident ends $12a_1$, $12a_2$ and $12a_3$ of the monitor optical fibers are arranged close to each other in a row to both directions orthogonal to the measurement plane $2p$ as shown in FIG. 6. Likewise, three measurement optical fibers can be used for each of receiving system and three incident ends of three measurement optical fibers are arranged close to each other in a row to both directions orthogonal to the measurement plane $2p$. With this arrangement, the quantity of received light can be increased without any significant influence on the measurement value. In this case, it is desirable that the aperture 13a of the light source aperture plate 13 in the illumination system 10 have a rectangular shape elongated to the both directions orthogonal to the measurement plane $2p$ so that the incident ends $12a_1$, $12a_2$ and $12a_3$ of the three monitor optical fibers can be well covered.

Figure 7:
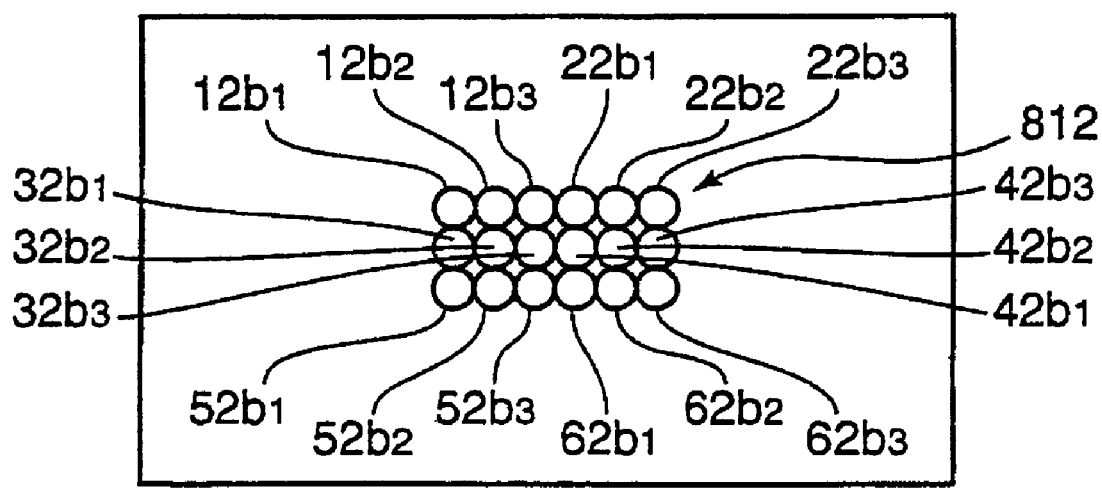
FIG. 7 shows still another example of the incident slit 81 of the spectroscope 80.

In this case, incident slit 812 of triple row arrangement in which the exit ends of the three optical fibers of each of the reference system and the light receiving system are arranged in the same row as shown in FIG. 7 is used. That is, the incident slit 812 is constructed as follows: The exit ends $12b_1$, $12b_2$ and $12b_3$ corresponding to the incident ends $12a_1$, $12a_2$ and $12a_3$ of the three monitor optical fibers 12 (see FIG. 6) are arranged in the first row and next thereto, the exit ends $22b_1$, $22b_2$ and $22b_3$ of the three optical fibers 22 for the first light receiving system 20 are arranged in the same row. In the similar manner, in the second row, the exit ends $32b_1$, $32b_2$ and $32b_3$ and the exit ends $42b_1$, $42b_2$ and $42b_3$ of the three optical fibers 32 and 42 for the second and third light receiving systems 30 and 40 are arranged, and in the third row, the exit ends $52b_1$, $52b_2$ and $52b_3$ and the exit ends $62b_1$, $62b_2$ and $62b_3$ Of the three optical fibers 52 and 62 for the forth and fifth light receiving system 50 and 60 are arranged.

In this case, the dispersed images of the incident slit of the first to third rows are positioned on the three adjoining pixels on the sensor array 84. Accordingly, the wavelength ranges of the incident lights are shifted by one or two pixels (10 or 20 nm, in this example). For example, when the wavelength ranges of the reference system and the first light receiving system 20 is 360 to 730 nm, those of the second light receiving system 30 and the third light receiving system 40 are 370 to 740 nm, and those of the fourth light receiving system 50 and the fifth light receiving system 60 are 380 to 750 nm. Therefore, the wavelength range of the multi-angle colorimeter S is 380 to 730 nm which is the range common for these ranges. Although the wavelength range is slightly reduced like this, the wavelength range necessary for colorimetry is sufficiently covered.

Figure 8:
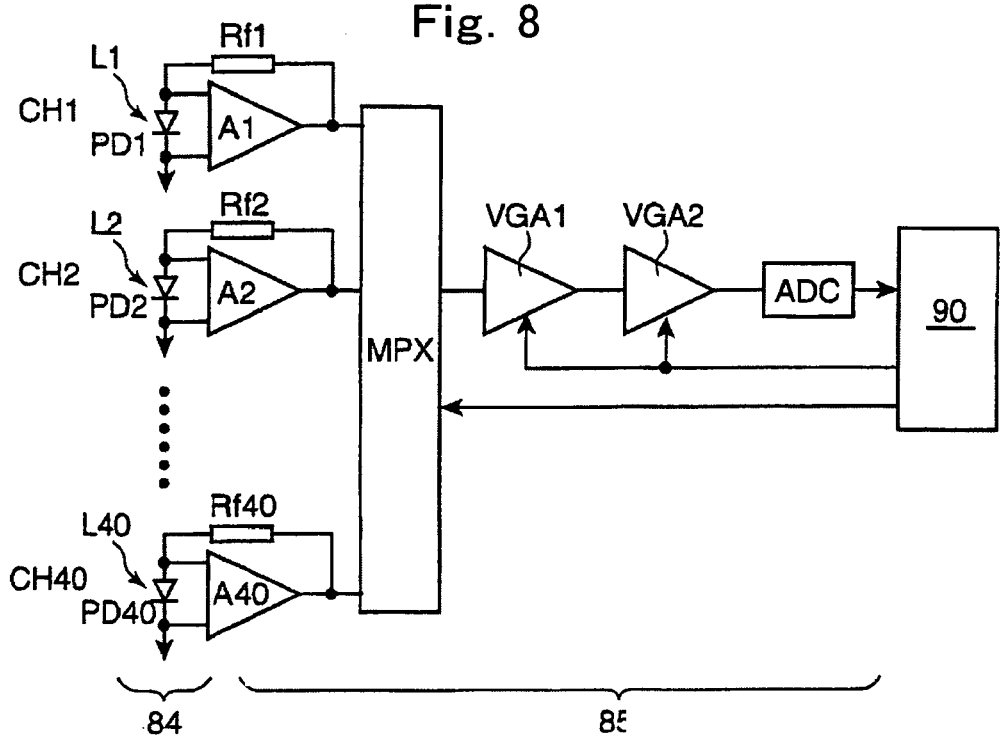
FIG. 8 is a block diagram showing an example of a signal processing circuit 85 in the spectroscope 80.

FIG. 8 is a block diagram of the signal processing circuit 85 including the sensor array 84. The signal processing circuit 85 has a current-to-voltage converting circuit An with the feedback resistor Rfn, a multiplexer MPX, a first variable gain amplifier VGA1, a second variable gain amplifier VGA2 and an analog-to-digital converter ADC.

The dispersed light (dispersed image of the incident slit) Ln incident on each pixel PDn (n=1 to 40, since the number of pixels is 40) of the sensor array 84 is converted into a current by a photodiode of each pixel PDn, and converted into a voltage signal by the current-to-voltage converting circuit An connected to each pixel PDn. The voltage signal of each pixel outputted from the current-to-voltage converting circuit An is successively selected by the multiplexer MPX controlled by the arithmetic control unit 90 and inputted to the 16-bit analog-to-digital converter ADC via the first and the second variable gain amplifier VGA1 and VGA2. The digital signal converted by the analog-to-digital converter ADC is transmitted to the arithmetic control unit 90.

The first variable gain amplifier VGA1 is for leveling the level differences of the signals outputted from the pixels PDn (the level differences among pixels of 10 nm interval). The level differences among pixels are leveled to some extent by providing the feedback resistor Rfn to the current-to-voltage converting circuit An suitable to the pixel (wavelength). However, by setting the gain of the first variable gain amplifier VGA1 suitable for the pixel selected by the multiplexer MPX, the level difference among pixels is further leveled. At the time of manufacture of the multi-angle colorimeter, the gain of each pixel PDn is selected so as to minimize the level differences, and stores as the gain data in a memory or the like provided in the arithmetic control unit 90 and at the time of measurement, the arithmetic control unit 90 reads a stored gain data for the pixel (wavelength) selected by the multiplexer MPX and set the gain by outputting a gain control signal.

The second variable gain amplifier VGA2 is an amplifier for leveling the level difference among the six incident lights from one reference system and five light receiving systems. That is, like the first variable gain amplifier VGA1, the gain of the second variable gain amplifier VGA2 is selected so as to minimize the level difference among six incident lights at the time of manufacturing. This gain is set based on the measurement of a highly diffuse and highly reflective standard sample, and the gain data is stored in a memory or the like provided in the arithmetic control unit 90. At the time of measurement, the arithmetic control unit 90 selects and sets a gain stored in the memory for the incident light selected by controlling the shutters 13 to 63.

Figure 9:
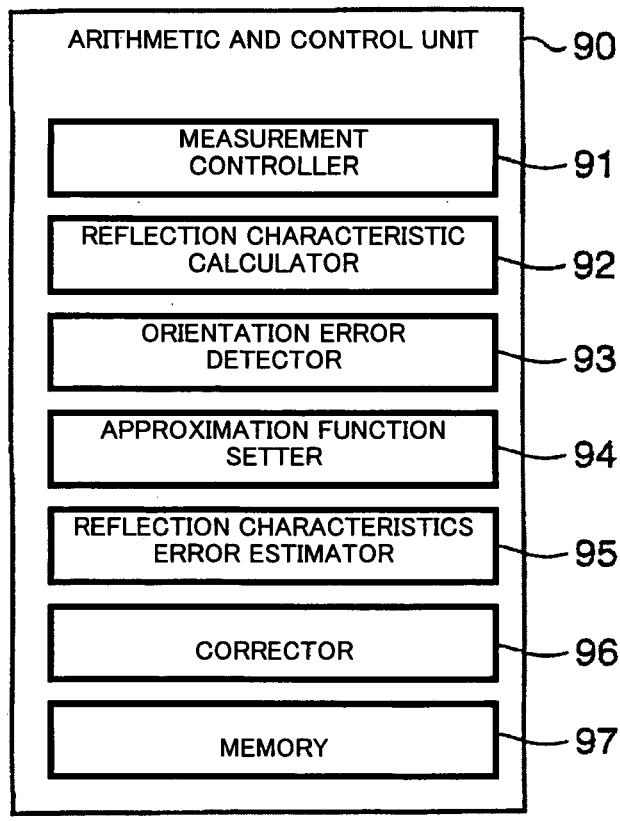
FIG. 9 is a functional block diagram showing the structure of an arithmetic control unit 90.

The arithmetic control unit 90 comprising a CPU and others controls the overall operation of the multi-angle colorimeter S. That is, the arithmetic control unit 90 controls the operation of each part of the multi-angle colorimeter for the calorimetric measurement of the sample surface 1, and performs the correction of the orientation error. FIG. 9 is a functional block diagram of the arithmetic control unit 90. The arithmetic control unit 90 has a measurement controller 91, a reflection characteristic calculator 92, an orientation error detector 93, an approximation function setter 94, a reflection characteristic error estimator 95, a corrector 96 and a memory 97.

The measurement controller 91 transmits a control signal to each part and controls the calorimetric measurement of the sample surface 1. Specifically, the measurement controller 91 supplies a control signal, corresponding to the operation sequence, to the light source driver 150 of the illumination system 10 to control the light source 15 and to the light source driver 74 of the illumination system 70 to control the light source 73. Moreover, the measurement controller 91 supplies a control signal to the shutter drivers 17 and 24 to 64 to control the shutters 16 and 23 to 63. For example, an operation is performed such that by opening one of the six shutters 23 to 63, the light flux passing through selected one of the reference system and the five light receiving systems (the first to fifth light receiving systems 20 to 60) is conducted to the spectroscope 80 and the spectral intensities thereof are measured. Further, the measurement controller 91 supplies a control signal to the spectroscope 80 to control the multiplexer MPX as mentioned above.

The reflection characteristic calculator 92 calculates the reflection characteristic of the sample surface 1 such as spectral reflection factor based on the intensity of the light reflected from the sample surface 1 illuminated by the illumination system 10 and received by the first to fifth light receiving systems 20 to 60. That is, the reflection characteristic calculator 92 calculates the reflection characteristic of the sample surface 1 for the reflection directions corresponding to the light receiving systems 20 to 60 based on the spectral data outputted from the spectroscope 80.

The orientation error detector 93 obtains the orientation error δ of the illumination system 10 and the first to fifth light receiving systems 20 to 60 with respect to the sample surface 1. The orientation error is detected by the orientation error detector 93 based on the reflected light intensity detected by a measurement system including the illumination system 70 that is different from the system for calorimetric measurement comprising the illumination system 10 and the first to fifth light receiving systems 20 to 60. The detection of the orientation error δ will be described later in detail.

The approximation function setter 94 determines the approximation function I(A) that approximates the direction dependence of the reflection characteristic based on the reflection characteristic obtained by the reflection characteristic calculator 92 and the orientation errors δ detected by the orientation error detector 93. The orientation error δ is an error is a degree of disagreement between the normal of the sample surface 1 and the reference axis $2n$ of the multi-angle colorimeter S, and accordingly the orientation errors δ is identical, that is, the degree and the direction of angular error is same for all of the first to fifth light receiving systems 20 to 60. Therefore, the approximation function I(A) is estimated by a least square method or the like using reflection characteristics obtained by the calculator 92 for the directions of the first to fifth light receiving systems 20 to 60 corrected by the uniform orientation error δ.

The reflection characteristic error estimator 95 estimates the reflection characteristic error in each receiving directions due to the orientation error δ based on the approximation function I(A) obtained. That is, the error in the measured reflection characteristics in each receiving direction is obtained as the difference ΔIm of values of approximation function I(A) calculated for the direction and deviated direction by the orientation error δ.

The corrector 96 corrects the measured reflection characteristic by the first to fifth light receiving systems 20 to 60, by use of the estimated reflection characteristic error ΔIm by the reflection characteristic error estimator 95. That is, the corrector 96 does not adopt the reflection characteristics calculated using the approximation function I(A) for the corrected direction as the reflection characteristics in the direction but corrects the measured reflection characteristics by use of the estimated error ΔIm obtained by use of the approximation function I(A).

The memory 97 comprised of a ROM, a RAM or the like stores the operation program of the arithmetic control unit 90 and temporarily stores measurement results and the like. In addition, the memory 97 stores the gain data to be supplied to the first and second variable gain amplifier VGA1 and VGA2.

Below, the operation of the multi-angle colorimeter S structured as described above will be described.

(Calculation of the Reflection Characteristics)

Figure 10:
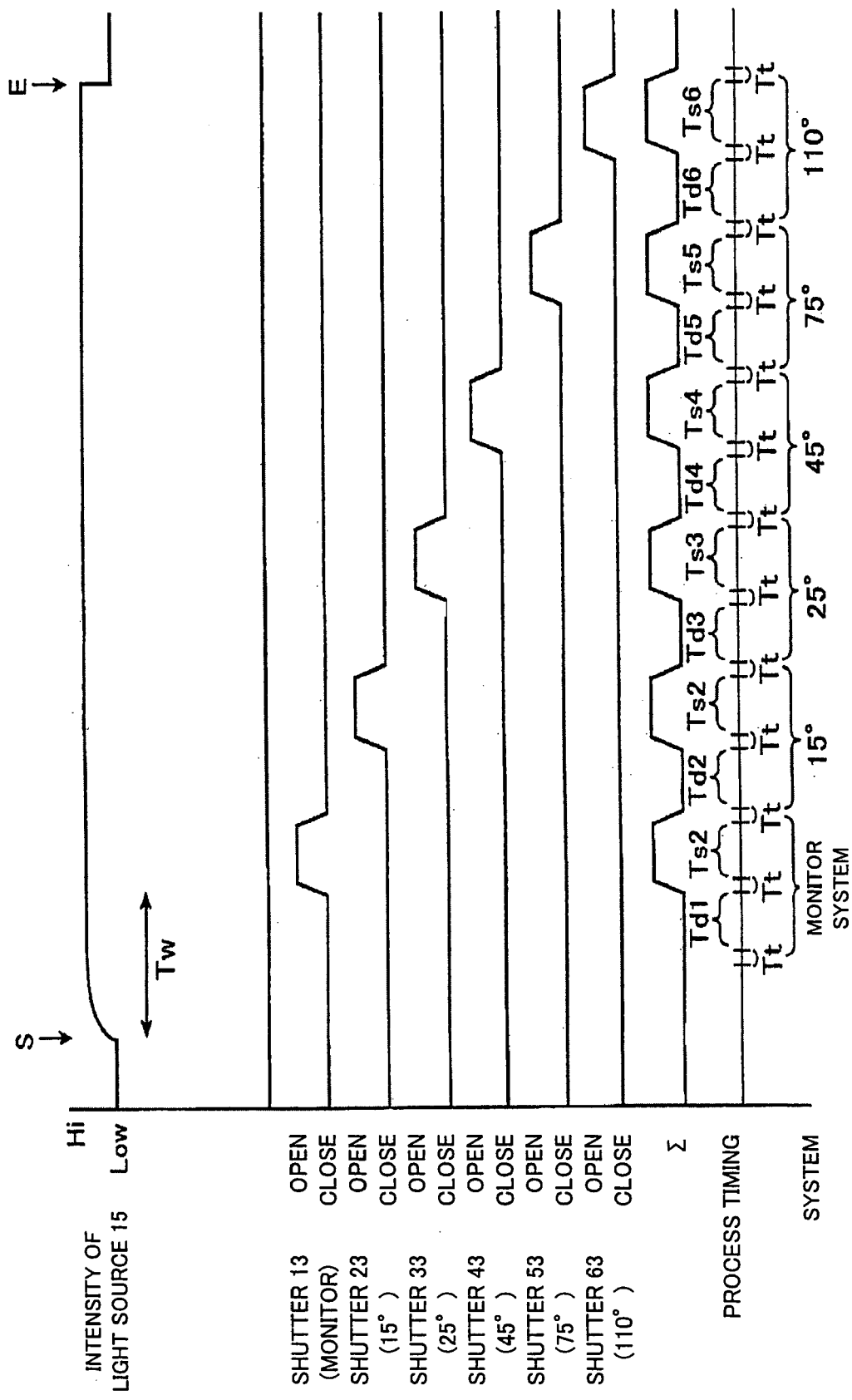
FIG. 10 is a timing chart for calculating reflectance factors.

A procedure for measuring the reflection characteristics (reflectance factor) will be described by use of the timing chart of FIG. 10. When receiving a start signal S, the measurement controller 91 turns on the light source 15 of the illumination system 10 via the light source driver 150. After the light source 15 is turned on, during a period Tw for the stabilization of the lamp, the shutter 16 of the reference system and the shutters 23 to 63 of the first to fifth light receiving systems 20 to 60 are all "closed". Therefore, in this stage, no light is incident on neither of the monitor optical fiber 12 of the reference system nor the measurement optical fibers 22 to 62 of the light receiving systems.

After the period Tw, the shutters 16 and 23 to 63 are successively "opened", and the monitor light and the reflected light from the sample surface 1 are measured. This measurement is first performed for the reference system, and then, performed successively for the first to fifth light receiving systems 20 to 60 (that is, in the order of 15, 25, 45, 75 and 110 degrees of aspecular angle). The measurement controller 91 of the arithmetic control unit 90 controls the shutter drivers 17 and 24 to 64 so that one of the shutters 13 to 63 is successively opened for a period Tsn, and measures the spectral intensity of the incident light from the corresponding system. That is, first, the shutter 16 is "opened" for a period Ts1, the monitor light is received by the incident end 12a of the monitor optical fiber 12 of the reference system, and the incident monitor light is directed to the spectroscope 80. Then, the shutter 16 is "closed" and the shutter 23 of the first light receiving system 20 is "opened" for a period Ts2, the reflected light from the sample surface 1 is received by the incident end 22a of the measurement optical fiber 22, and the incident light is directed to the spectroscope 80. Then, in the order of the second to the fifth light receiving system 30 to 60, the shutters 33 to 63 thereof are successively "opened" for periods Ts3 to Ts6, the reflected light from the sample surface 1 is received by the incident ends 32a to 62a of the measurement optical fibers 32 to 62, and the incident light is directed to the spectroscope 80.

Describing the measurement flow in further detail, prior to the shutter "open" period Tsn, an offset Dr (n) of each pixel channel (pixel PDn) of the sensor array 84 is measured in a period Tdn (offset measurement period Tdn) equal to the period Ts. The same gains as those in the succeeding shutter "open" period Tsn are set to the first and second variable gain amplifiers VGA1 and VGA2 in the offset measurement period Tdn. Between the offset measurement period Tdn and the shutter "open" period Tsn, a period Tt for the shutter stabilization is provided.

In the monitor light measurement, the offset Dr(n) of each pixel channel is measured during the lamp stabilization period Tw (or in the offset measurement period Td1) with the gain for the monitor light measurement. During the offset measurement, the measurement controller 91 controls the multiplexer MPX to successively select the pixel channels of the sensor array 84, sets the gains corresponding to the selected pixel channels in the first and second variable gain amplifiers VGA1 and VGA2 and store the output of the analog-to-digital converter ADC (pixel scanning). After this pixel scanning is repeated a predetermined number of times for averaging, the shutter 16 is "opened" for the period Ts1, and the monitor light is directed to the incident slit 81 of the spectroscope 80 through the monitor optical fiber 12. Then, similarly to the above-described offset measurement, pixel scanning is performed to measure the spectral intensity Sr(n).

Then, the shutter 16 is "closed", and similarly to the monitor light measurement, offset D1(n) is measured during the offset measurement period Td2 with the gain for the reflected light measurement by the first light receiving system 20. Then, the shutter 23 is opened during the shutter "open" period Ts2, and the reflected light from the sample surface 1 incident on the first light receiving system 20 is directed to the spectroscope 80 through the measurement optical fiber 22, and a spectral intensity S1(n) is measured. Likewise, offsets D2(n) to D5(n) and spectral intensities S2(n) to S5(n) for the second to fifth light receiving system 30 to 60 are successively measured.

When all the measurements are finished, the measurement controller 91 generates a measurement end signal E to turn off the light source 15 of the illumination system 10. Then, the reflection characteristic calculator 92 calculates the offset-corrected spectral intensity of the monitor light Qr(n) incident on the reference system by the following equation:

$Qr(n)=Sr(n)-Dr(n)$.

Moreover, the offset-corrected spectral intensity of reflected light Qm(n) of the incident light on the first to fifth light receiving systems 20 to 60 is corrected by the following equation:

$Qm(n)=Sm(n)-Dm(n)$ (here, $m=1$ to 5).

Further, the reflection characteristic calculator 92 calculates the reflectance factor Rm based on the spectral intensities Qr (n) and Qm(n) for the directions of the aspecular angles of 15, 25, 45, 75 and 110 degrees. The reflectance factors Rm of the sample surface are ratios of the measured spectral intensity Qm(n) in each direction to the spectral intensity Qwm ($m=1$ to 5) of a perfect reflecting diffuser equally illuminated and received and calculated by the following equation:

$Rm=Qm/Qwm$.

(Correction of the Orientation Error)

The above-described measurement of the reflectance factors Rm is premised on the coincidence of the reference axis 2n of the multi-angle colorimeter S and the normal 1n of the sample surface 1. A deviation of the reference axis 2n from the normal in causes an orientation error in the measured reflectance factors Rm and accordingly in calorimetric values. Therefore, the orientation error is removed from the reflectance factors Rm by a method described below.

Figure 11:
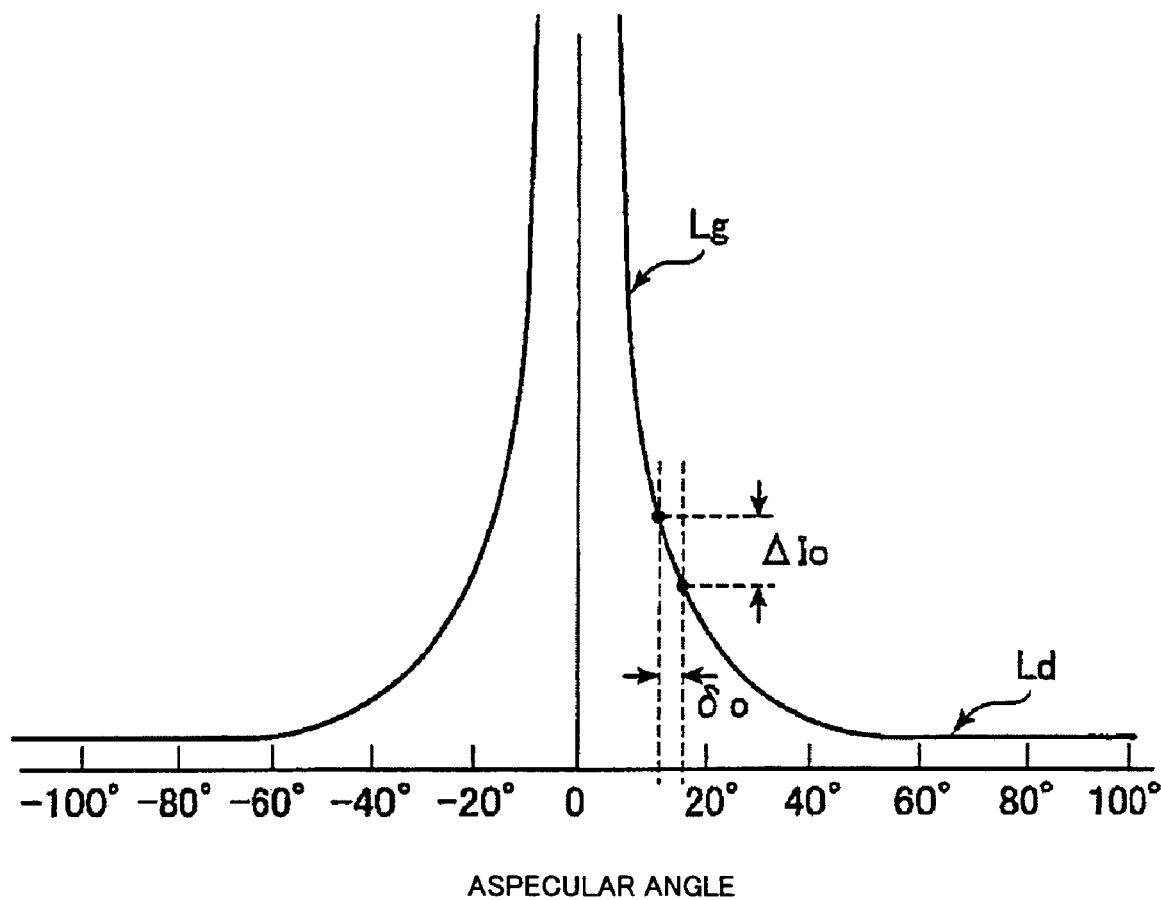
FIG. 11 is a graph showing an example of reflection characteristics.

FIG. 11 is a graph showing a directional dependence of a reflectance factor of coating containing special effect flake pigments such as metallic or pearlescent coating illuminated from one direction. Generally, the reflectance characteristic has a component by a specularly reflected light Lg from the sample surface 1 and a component by a diffusely reflected light Ld having no directional dependence.

Figure 12:
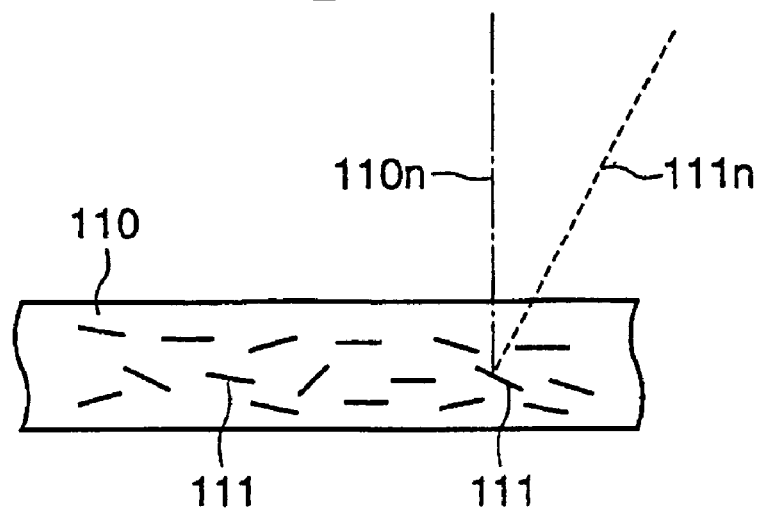
FIG. 12 is a cross-sectional view of a gonio-apparent coating 110, containing special effect pigments 111, to be measured.

As shown in FIG. 12, in coating layer 110 containing special effect flake pigments 111 (flake, hereafter), surfaces of flakes tend to be parallel to the coating surface (that is, the normal 111n of the surfaces of flakes 111 and the normal 110n of the coating 110 tend to be parallel) within the coating 110. And the angular distribution of the flake surfaces 111 within the coating layer 110 is close to a Gaussian distribution with the peak at t=0 (parallel to the coating surface). Here, t is the angle between the normal 111n of flake surface and the normal 11n of the coating surface. Therefore, when illuminated from a specific direction, the light reflected by the coating has the angular dependence close to a Gaussian distribution with the peak at the specular reflection direction.

Thus, the reflectance characteristic of the coating containing special effect flake pigments has an angular dependence such as shown in FIG. 11 within the measurement plane 2p which is particularly steep in the vicinity of direction of specular reflection. This means that the sensitivity to the orientation error is high in this region and an orientation error, if exists, results un-negligible measurement error. Therefore, an orientation error is corrected by the following steps:

(1) Step 1: Detection of the orientation error

The amount of orientation error is detected by the orientation error detector 93 by use of the illumination system 70 provided separately from the illumination system 10.

(2) Step 2: Approximation of the angular dependence of the reflectance factor by mathematical function.

The approximation function I(A) expressing the reflectance factor Rm ($m=1$ to 5) measured by the light receiving system in each direction as a function of the anormal angle Am is obtained by the approximation function setter 94.

(3) Step 3: Estimation of the reflectance factor error

A reflection characteristic error estimator 95 estimates the reflectance factor error in each direction due to the orientation error based on the approximation function I(A) obtained in the step 2.

(4) Step 4: Correction of the orientation error

A corrector 96 corrects the measured reflectance factor by use of the estimated reflectance factor error obtained at step 3.

The sensitivity of the reflectance factor to the orientation error is not high in the direction orthogonal to the measurement plane 2p in the vicinity of the reference axis 2n. FIG.

Figure 13:
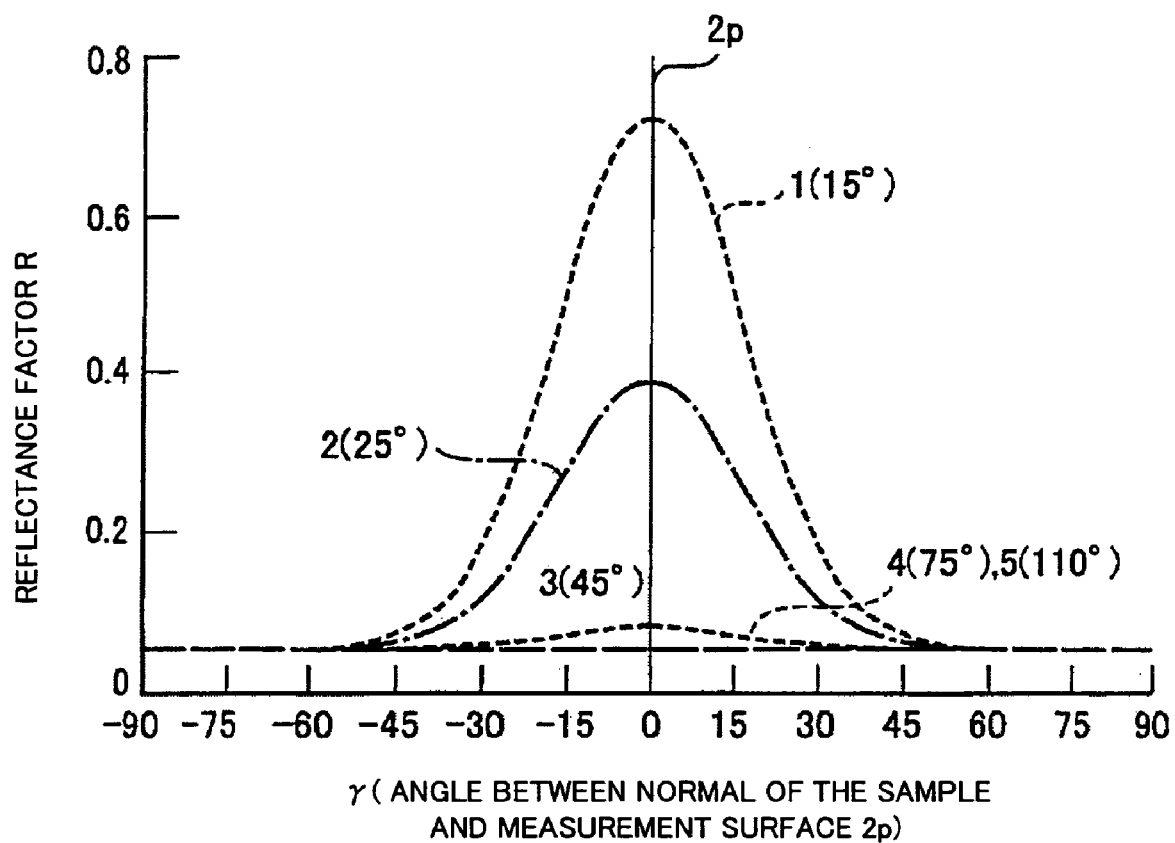
FIG. 13 is a graph showing an example of the reflection characteristic in the plane 2q orthogonal to the measurement plane 2p.

13 shows the dependence of reflectance factors detected by the first to fifth light receiving systems 20 to 60 on the tilting angle γ (an orientation error) in the measurement plane 2q, when the sample is illuminated by the illumination system 10 within the measurement plane 2p. As is apparent from FIG. 13, the sensitivity of the reflectance factor to the orientation error γ within the measurement plane 2q is negligible in the vicinity of the measurement plane 2p. Therefore, the influence thereof is negligible for any direction in the measurement plane 2p.

The above-mentioned steps 1 to 4 will be described in detail.

[Step 1: Detection of the Orientation Error]

As previously described with reference to FIG. 12, the orientation of the surface of the special effect flake pigments 111 can be approximated by a Gaussian distribution with the center at the direction parallel to the surface of the coating 110. Accordingly, the angular distribution of the reflected light by the special effect flake pigments 111 is close to Gaussian distribution with the peak at the direction of specular reflection by the surface of the coating 110 and expressed by the following Gaussian function G(Ap):

$$G(Ap) := G0 \cdot \exp\left[-\left(\frac{Ap - Ac}{\frac{dA}{2\sqrt{\ln(2)}}}\right)^2\right] \quad (1)$$

In the expression 1, Ap is the anormal angle within the coating 110, Ac is the anormal angle of the distribution center, $G_0$ is the peak intensity, and dA is the half intensity width.

In the case when measuring a gonio-apparent coating 110 as described above, the light reflected by the special effect flake pigments 111 within the coating 110 coating 110 and exited into the air has the primary role in observed angular dependence of reflectance characteristics. The light reflected is affected by the optical characteristic of the coating 110 at the boundary between the coating 110 and the air. That is, as shown in FIG. 14(a), when the sample is illuminated by illumination light g from a direction of 45 degrees of anormal angle as conventionally done, the influences of the asymmetric optical characteristics of the medium on both sides of the specular reflection direction are so large that a simple symmetric Gaussian function cannot accurately approximate the angular dependence.

That is, as shown in FIG. 14, the illumination light g is reflected in various directions by special effect flake pigments 111, 112 and 113 within the coating 110 having a surface parallel to the coating surface (111), tilted toward the illumination light g (112) and tilted toward the opposite side to the illumination light g (113) respectively and observed as the respective reflected lights h1, h2 and h3. However, the reflected lights h1, h2 and h3 are partly reflected back at the surface of the coating 110 (by Fresnel reflection) causing re-reflected lights h11, h21 and h31. While the direction of the illumination light g is fixed to 45 degrees, the directions of the reflected lights h1, h2 and h3 differ according to the direction of the special effect flake pigments, and accordingly, the angles of incidence on the surface of the coating 110 differ.

Figure 14A:
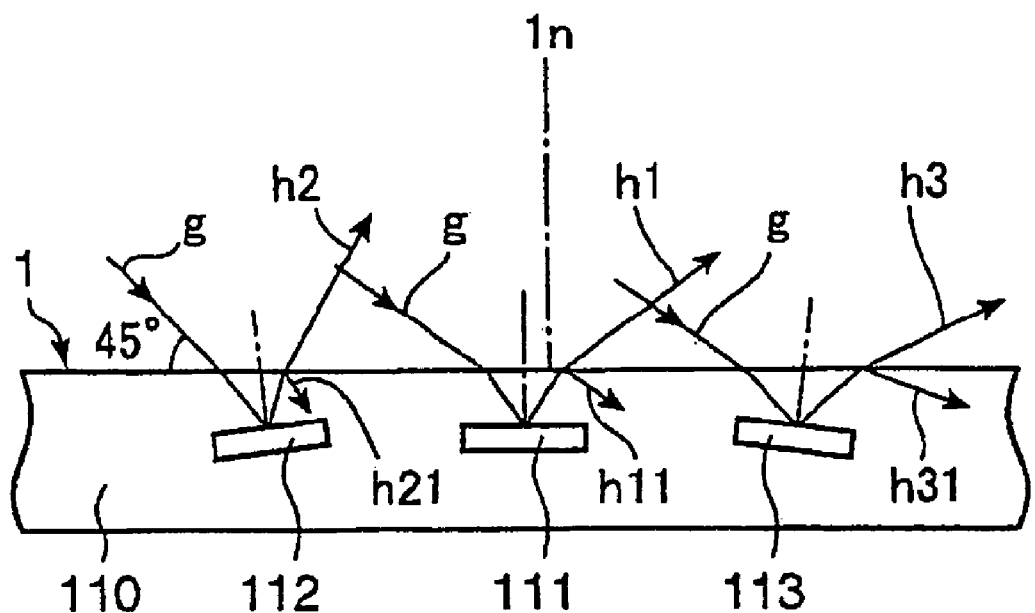
FIG. 14(a) is a schematic view showing reflections by flakes in the coating resulting the lights emanated to different directions from the sample surface 1 when illuminated from a direction of 45 degrees in anormal angle.
Figure 14B:
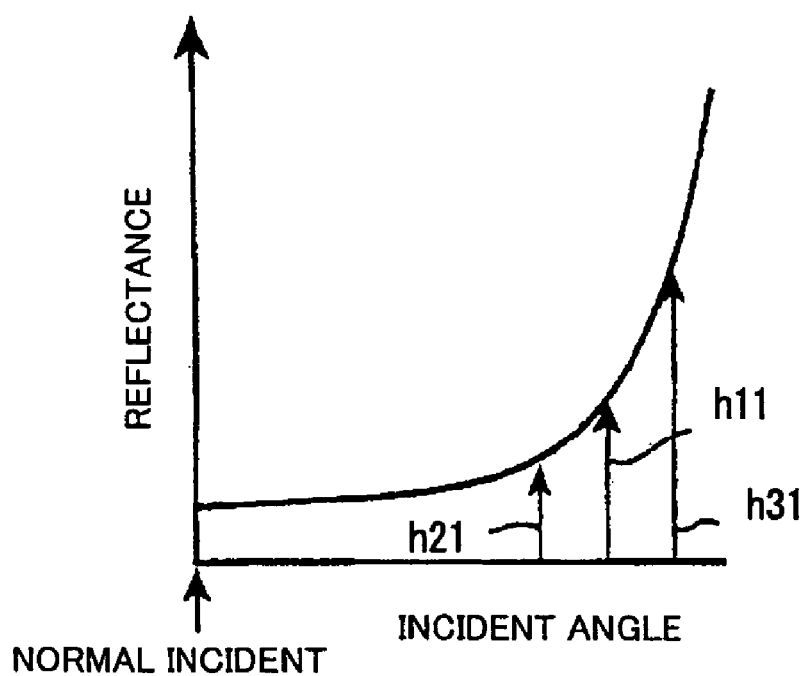
FIG. 14(b) is a graph showing the reflectance for lights of different incident angles on the surface.

As shown in FIG. 14(a), since the incident direction of light h2 on the surface is closer to the normal 1n than that of light h3, the reflectance for re-reflected light h21 at the surface is lower than that for the re-reflected light h31 (see FIG. 14(b)). As the result, the transmittance on the sample surface for light h2 is higher than that for the light h3, and they do not exhibit a symmetrical characteristic on both sides of the light h1 in the specular reflection direction. Even if a subsequently-described mathematical function considering the asymmetric optical characteristics based on Snell's law, Lambert's law, Fresnel reflection, the effective cross-section and the like is introduced into the approximation in order to correct the influence of the asymmetry, the estimated orientation error is not accurate enough.

Figure 15A:
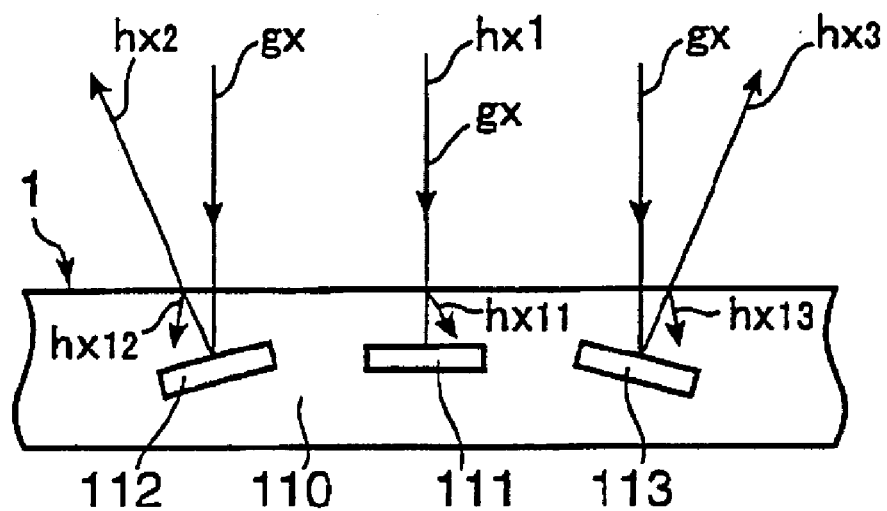
FIG. 15(a) is a schematic view showing reflections by flakes in the coating resulting the lights emanated to different directions from the sample surface 1 when illuminated from a direction close to the normal of the sample surface.

On the contrary, by comprising the colorimeter so that the illumination system 70 is disposed in a direction deviated from the normal 1n (reference axis 2n) of the sample surface by a small angle β within the measurement plane 2q and illuminates from the direction thereof, the optical characteristics of the medium on both sides of the specular reflection direction are substantially symmetrical. Moreover, by tilting the illumination system 70 by the angle β, the specularly reflected light Lg shown in FIG. 11 can be directed to the outside of the measurement plane 2p. That is, as shown in FIG. 15(a), when illuminating in the direction tilted by the angle β off the normal 1n in the measurement plane 2q, the illumination light gx is reflected by the special effect flake pigments 111, 112 and 113 within the coating 110 and the respective reflected lights hx1 to the direction of the normal 1n and hx2 and hx3 to both sides thereof exit to the air in the measurement plane 2p. At the boundary of the coating 110 and the air, a part hx11, hx21 or hx31 of each reflected light hx1, hx2 or hx3 is reflected back.

Figure 15B:
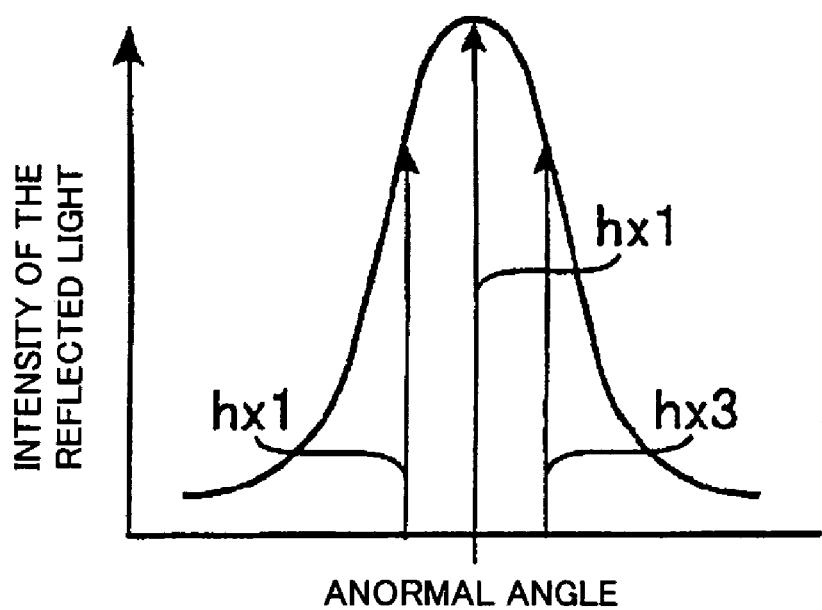
FIG. 15(b) is a graph showing the relative intensity of lights reflected in different anormal angles.

However, since all of the reflected lights hx11, hx21 and hx31 are in the directions not away from the normal 1n, there is no significant difference in the incident angles thereof and accordingly in the reflectance thereof at the boundary. Moreover, by using the first and fourth light receiving systems 20 and 50, the incident angles to the boundary of reflected lights hx2 and hx3 can be + and −30 degrees. Therefore, the boundary reflectance thereof has a negligible difference and can be treated as being the same. As the result, the angular distribution of the reflected light intensities from the sample surface 1 illuminated by the illumination light gx is substantially symmetrical on both sides of the specularly reflected light hx1 as shown in FIG. 15(b). Therefore, even a simple Gaussian function G'(A) can approximates the relationship between the reflected light intensity and the direction, and the orientation error can be accurately estimated from the distribution center thereof. While it is desirable for the direction of illumination light gx to be as close to the normal 1n (reference axis 2n), that is, the angle β to be as close to 0 degree as possible. It is also desirable for the specularly reflected light thereof not to be incident on the light receiving system (in the present embodiment, on the third light receiving system 40). Therefore, the angle β is preferably 5 to 25 degrees, particularly preferably 10 to 20 degrees. The Gaussian function G'(A) described above is expressed by the equation (2) below:

$$G'(A) := G0 \cdot \exp\left[-\left(\frac{Ap - A}{\frac{dA}{2\sqrt{\ln(2)}}}\right)^2\right] + d \quad (2)$$

In the equation (2), A is the anormal angle in the air. Anormal angles in the paint used in the equation (1) can be converted to those in the air by the equation (8) of Snell's law described later.

As described above, as the optical axis of the illumination system 70 (see FIG. 2(b)) containing the reference axis 2n is shifted from the measurement plane 2p by the predetermined angle β in the measurement plane 2q orthogonal to the measurement plane 2p, the specularly reflected light 70a of the sample surface 1 is not incident on the first to fifth light receiving systems 20 in the measurement plane 2p, but the reflected lights from the special effect flake pigments 111 within the coating 110 are incident on the light receiving systems 20 to 60.

Figure 16:
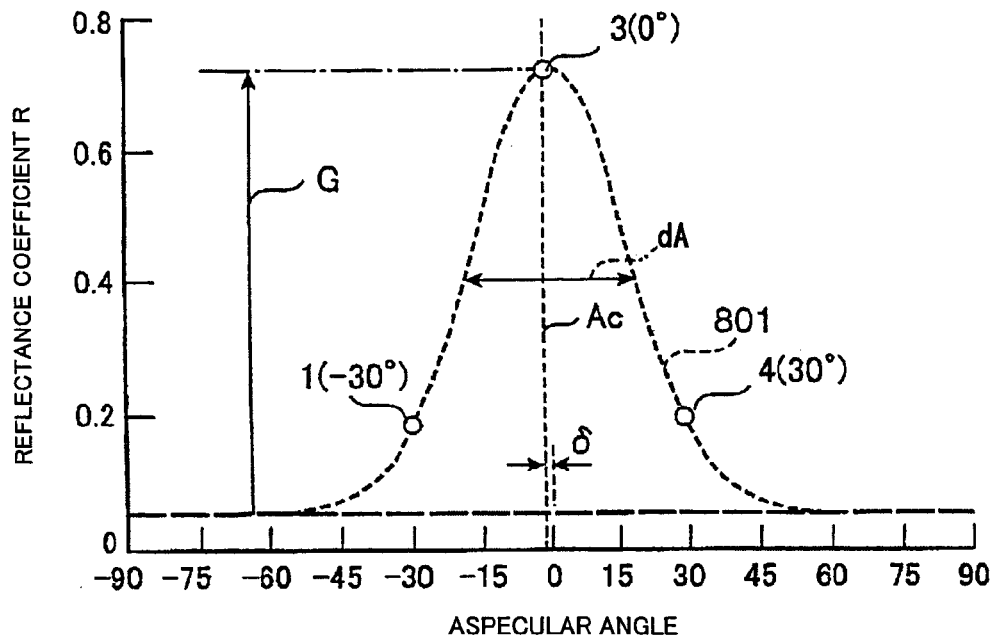
FIG. 16 is a graph showing a Gaussian function used for orientation error detection.

The measurement controller 91 controls the light source driver 74 to turn on the light source 73 for illuminating the sample and the reflected light thereby is measured by the first, third and fourth light receiving systems 20, 40 and 50. Then the light intensities Q1, Q3 and Q4 are obtained by the reflection characteristic calculator 92. Then, as shown in FIG. 16, a simple Gaussian function (801 in FIG. 16) that best approximates the relationship between the light intensities Q1, Q3 and Q4 (o's in FIG. 16) and the anormal angles A1 (−30 degrees), A3 (0 degrees) and A4 (+30 degrees) of the light receiving systems 20, 40 and 50 is obtained by the least squares method. That is, the peek height $G_0$, distribution center Ac and half height width dA resulting the least sum of squares of the residual error calculated by the following equation (3) are obtained by the orientation error detector 73:

$$Er(G_0, dA, Ac) := \sum_m (G(Am) - Qm)^2 \qquad (3)$$

$$m = 1, 3, 4$$

The orientation error δ is given by the distribution center Ac of the obtained simple Gaussian function 801. Since the distribution center Ac is not dependent on the wavelength, a monochromatic LED can be used as the light source 73 of the illumination system 70.

[Step 2: Approximation of the Angular Characteristics of the Reflectance Factor by Mathematical Function]

Subsequently, the approximation function I(A) expressing the reflectance factor Rm (m=1 to 5) measured by the light receiving systems 20 to 60 with the illumination by the illumination system 10, as a function of the anormal angle Am is obtained by the approximation function setter 94 on the basis of the simple Gaussian function.

The approximation function I(A) is determined by the peak I0, the distribution center Ac, the half height width dA, a diffuse reflection factor d and the refractive index np of the coating 110. The refractive index np is specific to the material of the coating 110 and can be inputted and stored in the memory 97 according to the coating 110 used. However, since the refractive indices of materials generally used for coating is quite similar, the average value of the refractive indices can be stored in the memory 97.

The distribution center Ac is given by correcting the specular reflection direction (−$A_0$, −45 degrees here) of the incident direction ($A_0$, 45 degrees here) of the illumination light by the orientation error δ detected by the orientation error detector (see FIG. 16) as expressed in the following equation (4):

$$Ac = -A_0 + \delta \qquad (4)$$

The remaining three constants $I_0$, dA and d are determined by the least squares method so that the sum of squares of the differences by the following equation (5) between the measured reflectance factors Rm (m=1 to 5) in the five reflection directions and the calculated values I(Am) by the approximation function is minimum:

$$Er(I_0, dA, d) := \sum_{m=1}^{5} (I(Am) - Rm)^2 \qquad (5)$$

The Gaussian function (802 in FIG. 17) represents the obtained approximation function I(A).

[Step 3: Estimation of the Reflectance Factor Error]

The reflection characteristic error estimator 95 estimates the error in the reflectance factor in each direction due to the orientation error δ based on the approximation function I(A) obtained at the above-described step 2. That is, by using the approximation function I(A) obtained by the approximation function setter 94, the reflection characteristic error estimator 95 calculates the deviation of the estimated reflectance factor when the viewing direction is deviated by the orientation error δ as the estimated error in each of the measured reflectance factors Rm (m=1 to 5).

Figure 17:
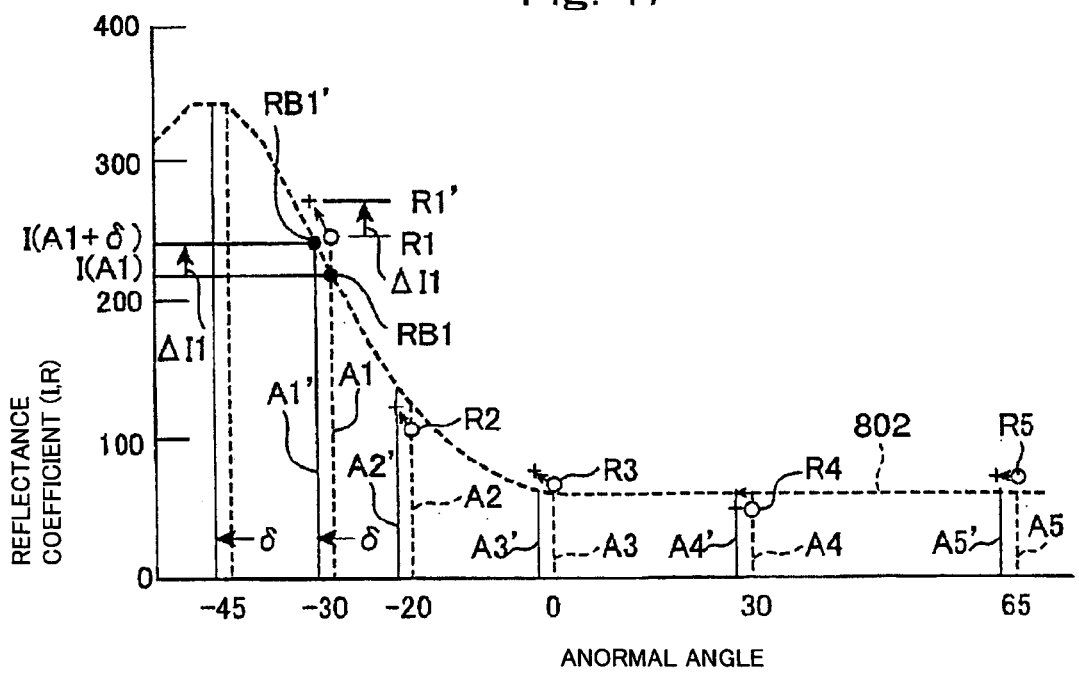
FIG. 17 is a graph for explaining the orientation error correction by an approximation function.

Describing with reference to FIG. 17, first the values of the approximation function I(Am) for the anormal angle Am (m=1 to 5) of each receiving direction for the reflectance factors R1 to R5 and the values of the approximation function I(Am') for the deviated anormal angle Am' from Am by the orientation error δ is calculated. Next, the difference of I(Am') at deviated direction from I(Am) at the original is calculated as the estimated error. Specifically in FIG. 17, a point RB1 on the approximation function I(A) at the anormal angle A1 (−30 degrees) and a point RB1' on the approximation function I(A) at the anormal angle A1' deviated by the orientation error δ are obtained, and the difference between the point RB1 and the point RB1' is obtained as the estimated error of the reflectance factor. Likewise, points at the anormal angles A2 (−20 degrees), A3 (0 degree), A4 (30 degrees) and A5 (65 degrees), and points at the anormal angles A2' to A5' deviated from A2 to A5 by the orientation error δ respectively are similarly obtained, and the error of the reflectance factor in each viewing direction is estimated. That is, I(Am) at the anormal angle Am for each receiving direction and I(Am+δ) at the corrected anormal angle are calculated based on the approximation function and then, the difference ΔIm therebetween is obtained by the following equation (6):

$$\Delta Im = I(Am+\delta) - I(Am) \qquad (6)$$

The thus obtained ΔIm is set as the estimated error of the reflectance factor.

[Step 4: Correction of the Orientation Error]

The corrector 96 corrects the actually measured reflectance factors R1 to R5 in each direction by use of the estimated reflectance factor error ΔIm obtained at step 3 based on the following equation (7):

$$Rm' = Rm + \Delta Im \qquad (7)$$

Describing with reference to FIG. 17, regarding angle A1 (−30 degrees) specifically, the estimated error ΔI1 of the reflectance factor due to the orientation error δ is obtained by the equation (6): ΔI1=I(A1+δ)−I(A1).

The measured value R1 at angle A1 (−30 degrees) is corrected by use of the estimated error ΔI1 by the equation (7) R1'=R1+ΔI1. The measured values R2 to R5 in the other receiving directions A2 to A5 are corrected in the same manner.

That is, the corrector 96 does not use the values I(Am+δ) of approximation function I(A) at the corrected anormal angles Am+δ as the corrected reflection characteristic but use the deviations ΔIm calculated based on the approximation function I(A) as estimated reflection factor error to correct each reflectance factors actually measured. Since the correction amount (ΔIm) is very small compared to the actual measurement value Im itself, the influence of the insufficient accuracy in approximation by approximation function is relatively small even if it is the case, and the correction is sufficiently effective. While the corrected aspecular angle Am+δ coincides with the nominal aspecular angle, the angle of incidence is still deviated from the nominal angle by the orientation error δ. However, since the angular dependence of the reflectance factor of the coating 110 containing the special effect flake pigments 111 is predominantly the dependence on the specular angle and the small deviation of the incidence angle bring a negligible influence.

By the above-described steps 1 to 4, the reflectance factors with the influence of the orientation error δ effectively removed is obtained.

Figure 18:
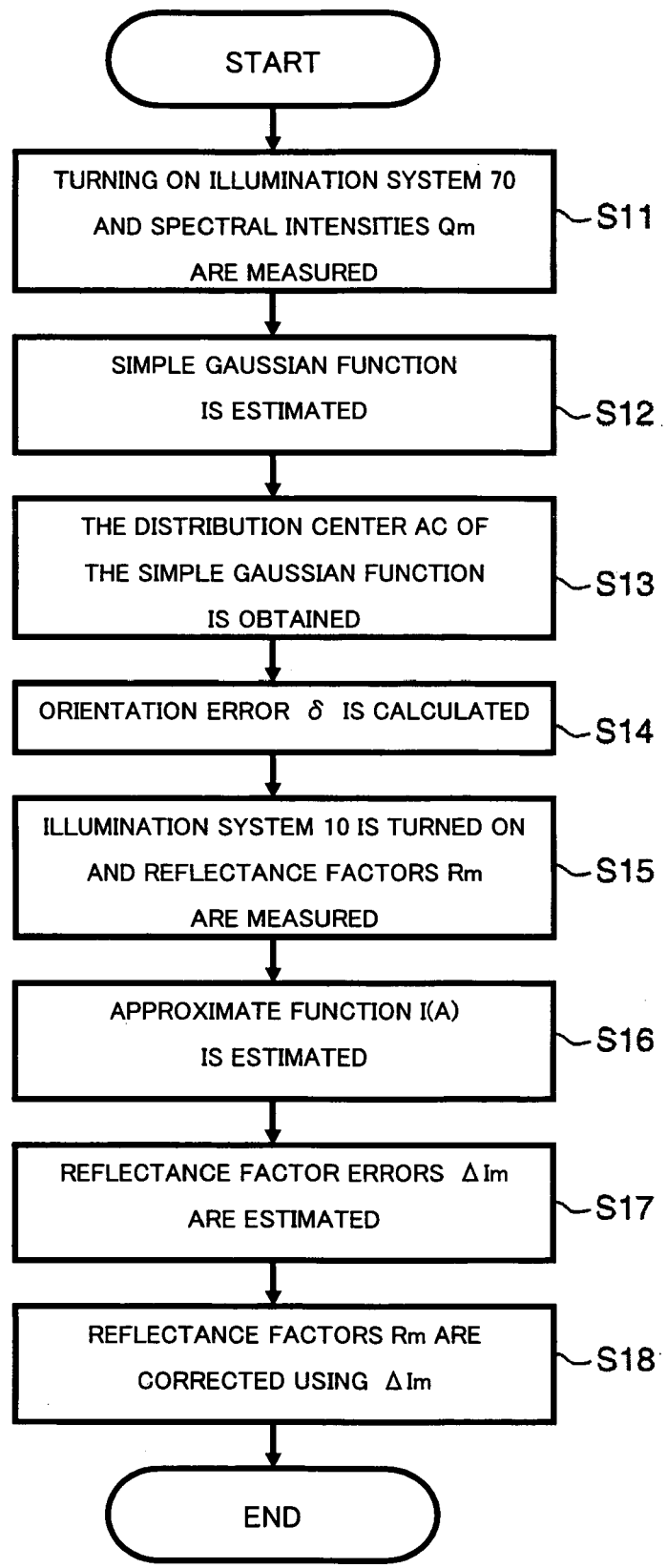
FIG. 18 is a flowchart of a measurement by the multi-angle colorimeter S including the orientation error correction.

FIG. 18 is a flowchart of the measurement by the multi-angle colorimeter S provided with the above-described orientation error correction. First, the illumination system 70 is turned on, the reflected light is measured by the first, third and fourth light receiving systems 20, 40 and 50, and the light intensities Q1, Q3 and Q4 (Qm) are obtained by the reflection characteristic calculator 92 (step S11). Then, the orientation error detector 93 determines the simple Gaussian function best approximating the relationship between the light intensities Q1, Q3 and Q4 (o's in FIG. 16) and the anormal angles A1=−30 degrees, A3=0 degree and A4=+30 degrees (Am) of the light receiving systems 30, 40 and 50 by a least square method with the above-described equation (3) (step S12). Then, the anormal angle of the distribution center Ac thereof is obtained (step S13) as the orientation error δ (step S14).

Then, the illumination system 10 is turned on, the reflected light from the sample surface 1 is received by the first to fifth light receiving systems 20 to 60, and the reflectance factors Rm (R1 to R5) are obtained (step S15). Then, to correct the orientation error, the approximation function I(A) expressing the obtained reflectance factors Rm as a function of the anormal angle Am is obtained by the approximation function setter 94 (step S16). Then, the estimated error of the reflectance factor ΔIm is obtained based on the approximation function I(A) (step S17). By use of the estimated error ΔIm, the measured reflectance factors Rm are corrected by the corrector 96 (step S18). In this manner, the measurement data with the influence of the orientation error δ removed is obtained.

In the above-described embodiment, the approximation function setter 94 approximates the angular distribution of the reflectance factor by the Gaussian function of the above-described equation (1) used for approximating the angular distribution of the special effect flake pigments. However, the approximation accuracy can be improved by introducing following four supplementary functions (a) to (d) to the Gaussian function of the equation (1):

(a) Snell's Law

Figure 19:
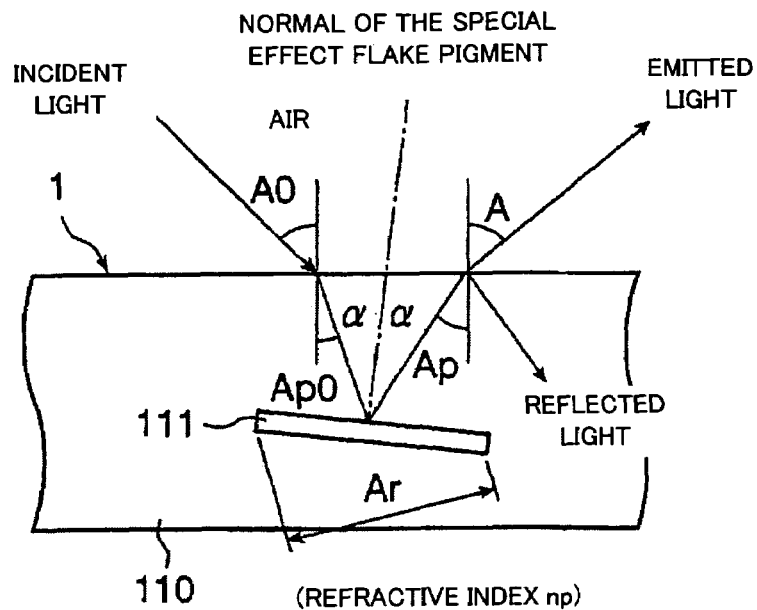
FIG. 19 is a schematic view showing the reflection of incident light by a flake 111 contained in the coating 110.

As shown in FIG. 19, the anormal angle A in the air and the anormal angle Ap in the coating are correlated by the Snell's law expressed by the following equation (8) where $n_p$ is refractive index of the coating 110 (medium):

$$Ap := a\sin\left(\frac{\sin(A)}{n_p}\right) \qquad (8)$$

(b) Lambert's Law

The reflectance factor measured by the multi-angle colorimeter S is the ratio of a reflected light from the sample surface illuminated and received under a certain condition to a reflected light from a perfect diffuser illuminated and received under the same condition. The intensity of the reflected light from a unit area of a perfect reflecting diffuser (Lambertian surface) to the direction of anormal angle A is proportional to cos(A). Therefore, when converting the reflected light intensity to the reflectance factor, it is necessary to take the Lambertian characteristics of a perfect reflecting diffuser by multiplying by the function Lm (A) shown in the following equation (9):

$$Lm(A) := \frac{1}{\cos(A)} \qquad (9)$$

(c) Fresnel Reflection

The light flux reflected by the special effect flake pigments 111 and directed to the outside of the coating 110 is partly reflected at the boundary between the coating 110 and the air (Fresnel reflection), and the remainder exits to the outside. The Fresnel reflection is dependent on the refractive index $n_p$ of the coating 110 and the incident angle Ap on the boundary. Accordingly the boundary transmittance Fr (Ap) of the light incident on the boundary at the incidence angle Ap is also dependent on the refractive index $n_p$ and the incidence angle Ap as expressed by the following equation (10):

$$Fr(Ap) := 1 - \frac{1}{2} \cdot \left[ \left[ \frac{\frac{n_p}{\cos(Ap)} - \sqrt{1 - (n_p \cdot \sin(Ap))^2}}{\frac{n_p}{\cos(Ap)} + \sqrt{1 - (n_p \cdot \sin(Ap))^2}} \right]^2 + \left[ \frac{\cos(Ap) - n_p \cdot \sqrt{1 - (n_p \cdot \sin(Ap))^2}}{\cos(Ap) + n_p \cdot \sqrt{1 - (n_p \cdot \sin(Ap))^2}} \right]^2 \right] \qquad (10)$$

(d) Effective Cross-sectional Area

As shown in FIG. 19, among all special effect flake pigments, only those in a direction $Ap_0+Ap$ reflect the incident light in a direction $Ap_0$ to the direction of the angle Ap of anormal angle within the coating. Therefore, the reflected light intensity is dependent not only on the concentration of special effect flake pigments 111 in this direction which is the angular distribution of the flakes 111, but also on the effective reflection area of the flakes 111 in the direction. Since the surface of the special effect flake pigments 111 contributing to the reflection to the direction Ap is, as shown in the figure, tilted by $(Ap-Ap_0)/2$ with respect to the incident direction $Ap_0$ within the coating 110, the effective reflection area Ar is proportional to $\cos(Ap-Ap_0)/2$, and expressed by the following equation (11):

$$Ar(Ap) := \cos\left(\frac{Ap - Ap_0}{2}\right) \qquad (11)$$

The approximation accuracy can be improved by correlating the anormal angles in the air and in the coating 110 by the above-described equation (8) based on Snell's law and by using the following function (12) that reflects the equations (9), (10) and (11) together with the equation (1), which expresses the angular distribution of the reflected light simply by the angular distribution of the special effect flake pigments 111. It is unnecessary to introduce all of supplemental functions reflecting above-described effects (a) to (d); the approximation accuracy can be improved by adding at least one of these supplemental functions.

$$I(A):=I_0 G(Ap)\cdot Lm(A)\cdot Fr(Ap)\cdot Ar(A)+d \quad (12)$$

In the equation (12), d is the reflectance factor due to the diffuse reflection within the coating 110. The reflectance factor d has no direction dependence, and is fixed with respect to an anormal angle A.

Figure 20:
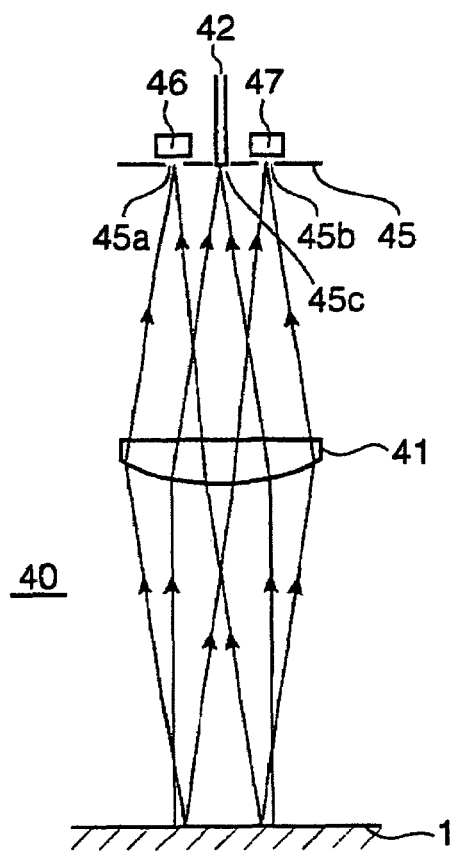
FIG. 20 is a structural view showing another example of an orientation error detector.

In the above-described embodiment, the illumination light by the illumination system 70 is received by the first, third and fourth light receiving systems 20, 40 and 50 which are provided for reflectance factor measurement. However, light receiving sensors for orientation error detection may be provided separately from the light receiving systems for reflectance factor measurement. FIG. 20 shows an example in which the above-mentioned light receiving sensors 46 and 47 are provided in the third light receiving system 30 whose anormal angle is 0 degrees.

In FIG. 20, an aperture plate 45 having three apertures 45a, 45b and 45c are disposed at the imaging position of the collimator lens 41. The measurement optical fiber 42 is disposed in the aperture 45c in the center of the aperture plate 45, and the light sensors 46 and 47 are disposed behind the apertures 45a and 45b on the both sides thereof. The current outputs of the two light receiving sensors 46 and 47 are processed by a non-illustrated current-to-voltage converting circuits, converted into digital signals by an AD converter, and transmitted to the arithmetic control unit 90.

With the structure described in FIG. 20, three light receiving elements comprising which are the incident end of the measurement optical fiber 42 and two light sensors 46 and 47 can be positioned at the aspecular angles of approximately 0 and ±10 degrees where sensitivities to orientation errors is very high. Consequently, the orientation error can be detected with high accuracy. Since the orientation of the reflected light by the special effect flake pigments is not dependent on the wavelength as mentioned above, silicon photodiodes or the like can be disposed as the light sensors 46 and 47 for orientation error detection.

Second Embodiment

Correction of the Initial Angular Error

As described above, when measuring the coating 110 containing the special effect flake pigments 111 by the multi-angle colorimeter S, since the reflection characteristic of the coating 110 is highly directional dependent, not only the orientation error described above but also an error in the aspecular angle of each light receiving direction the multi-angle colorimeter S initially has, bring about an error in the reflection characteristics measurement. For this reason, it is desirable to manufacture a multi-angle colorimeter S with the initial angular error as close to zero as possible. However, in actuality, the light receiving directions unavoidably deviates from the nominal directions due to various manufacturing errors, and the initial angle error is inevitable. In particular, the initial angle error brings about a significant reflection characteristic error in the receiving direction close to the specular reflection direction where the sensitivity to angular error is high. Consequently, the initial angular error is a primary cause of the geometry error. Therefore, in the multi-angle colorimeter S according to this embodiment, the initial angular error is corrected by the following steps S21 to S24:

[Step 21] Measurement of the Actual Aspecular Angle (Actual Anormal Angle)

At the time of manufacturing the multi-angle colorimeter S, the actual aspecular angles Bm (m=1 to 5) of the light receiving directions are measured, and converted into the actual anormal angle Am by Am=Bm−45. The initial angular errors of the first to fifth light receiving systems 20 to 60 are obtained therefrom. For this, a rotatable reference reflecting surface is placed at the position of a sample surface 1 and thereby the specular reflection direction of the illumination light is variable in the measuring plane 2p. The intensity of reflected light Om is measured by the light receiving systems 20 to 60 at varying specular reflection direction, and therefrom the initial angular errors are obtained.

[Step S22] Approximation of the Angular Dependence of the Reflectance Factor of the Sample by Mathematical Function The approximation function setter 94 determines the approximation function I(A) approximating the reflectance factor Rm (m=1 to 5) measured by the light receiving system in each direction as a function of the actual anormal angle Am.

[Step S23] Estimation of the Reflectance Factor Error

The reflection factor error estimator 95 calculates the reflectance factor at the actual anormal angle including the initial angle error in each light receiving direction and those at the nominal anormal angle based on the approximation function I(A) obtained at the above-described step S22 and calculates the difference therebetween as the estimated reflectance factor error due to the initial angular error.

[Step S24] Correction of the Initial Angular Error

The corrector 96 corrects the actual measured reflectance factors by use of the estimated reflectance factor errors obtained at step 23. The detail of the above-mentioned steps S21 to S24 will be described in succession.

Figure 21:
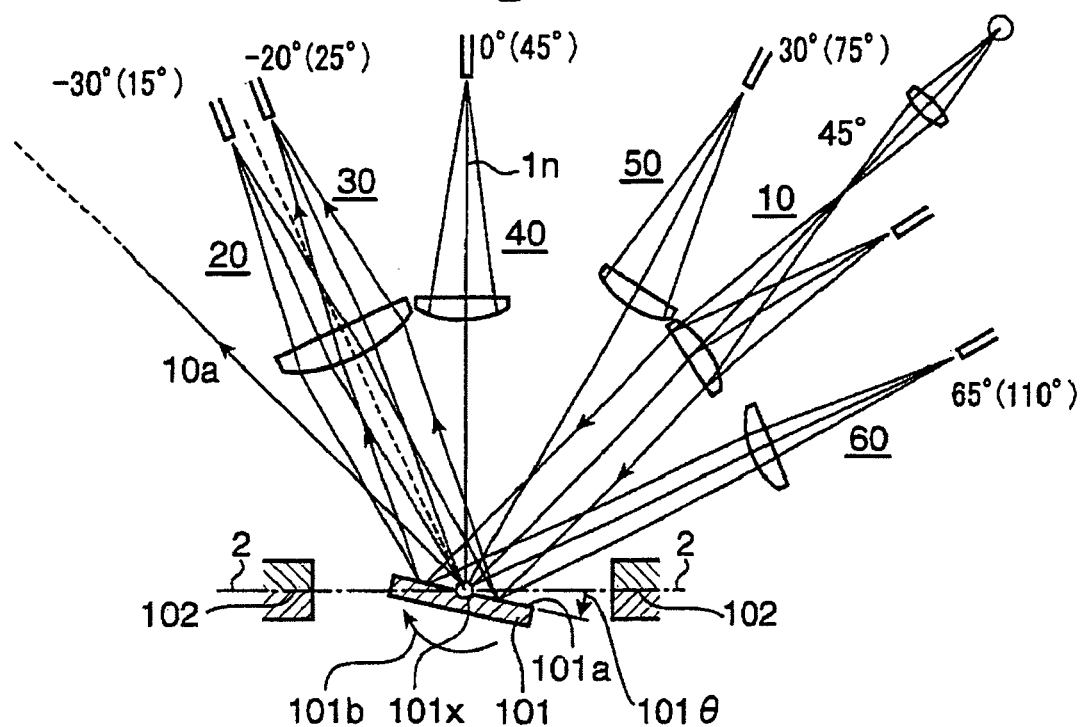
FIG. 21 is a cross-sectional view in the measuring plane showing the structure of a system for measuring initial angle errors.
Figure 22:
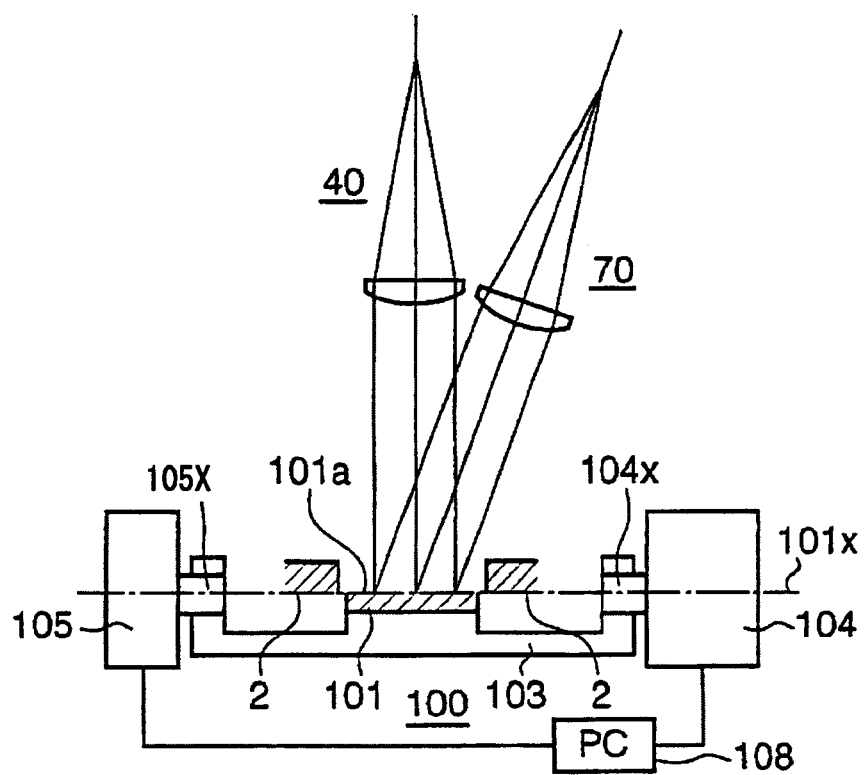
FIG. 22 is a cross-sectional view in the plane orthogonal to the measuring plane showing the structure of a system for measuring initial angle errors.

As shown in FIGS. 21 and 22, a jig 100 having a reference reflecting surface whose direction is variable is used for measuring the actual anormal angles. The jig 100 is provided with a reference surface 102 that is in contact with the measurement aperture surface 2 of the multi-angle colorimeter S (see FIG. 1) and a glass plate 101 rotatable about a rotation axis 101x which is within the reference surface 102 and vertical to the measurement plane 2p of the multi-angle colorimeter S. The glass plate 101 has a reference reflecting surface 101a containing the rotation axis 101x. The glass plate 101 preferably a black glass plate for eliminating the influence of the reflection by the rear surface.

As shown in FIG. 22, the black glass plate 101 is fixed to the rotation axis 101x by the support member 103. The black glass plate 101 rotates to the directions shown by arrow 101b in FIG or the reverse direction by a pulse motor 104 having a rotation axis 104x that is concentric with the rotation axis 101x. The rotation of the pulse motor 104 is controlled by a control PC 108 connected for controlling the jig 100. Moreover, the rotation angle 101Θ of the black glass plate 101 is detected by a rotary encoder 105 attached to the support member 103 and having a rotation axis 105x that is concentric with the rotation axis 101x. The output (angle output W) of the rotary encoder 105 is read out by the control PC 108.

Figure 23:
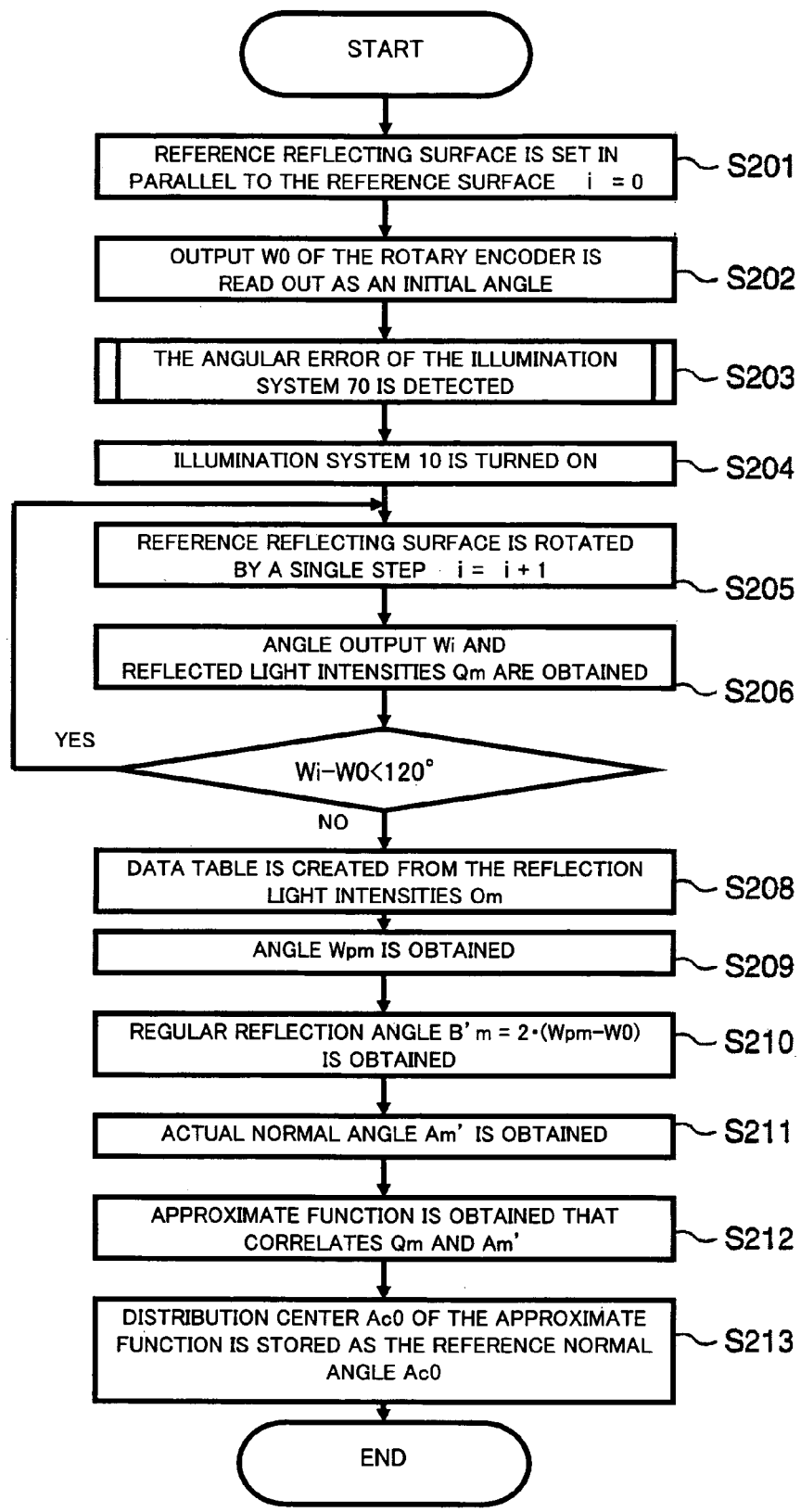
FIG. 23 is a flowchart of the measurement of actual anormal angles at the time of manufacturing.

FIG. 23 is a flowchart showing an operation at the time of manufacture including the measurement of the actual anormal angle. First, prior to the measurement of the actual anormal angle, the reference reflecting surface 101a is set in parallel to the reference surface 102 (step S201). The direction of the reflected light at this time is the specular reflection direction, and the output of the rotary encoder 105 is read out by the control PC 108 as an angle W0 of the specular reflection direction (step S202) and the rotary encoder 105 is initialized. Then, the multi-angle colorimeter S to be corrected is placed so that the measurement aperture surface 2 is in contact with the reference surface 102 and the measurement plane 2p is orthogonal to the rotation axis 101x. Then, the multi-angle colorimeter S is also connected to the control PC 108 for controlling the operation thereof and receiving the measurement data therefrom. Subsequently thereto, the angle error of the illumination system 70 is detected at step S203 as described later.

The control PC 108 turns on the illumination system 10 of the multi-angle colorimeter (step S204). Then, the control PC 108 controls the pulse motor 104 to rotate the reference reflecting surface 101a in the direction of 101b by a predetermined small step of angle (step S205). The light flux from the illumination system 10 is reflected by the reference reflecting surface 101a at the position and the control PC 108 receives and stores the reflected light intensities Om (m=1 to 5) received by the five light receiving systems 20 to 60 together with an angle output Wi of the rotary encoder 105 (step S206). These steps S205 and 206 are repeated until the aspecular angle reaches 120 degrees ('No' at step S207), that is, until the difference Wi−W0 between the angle output Wi of the rotary encoder 105 and the angle W0 in the specular reflection direction becomes 120 degrees.

Figure 24:
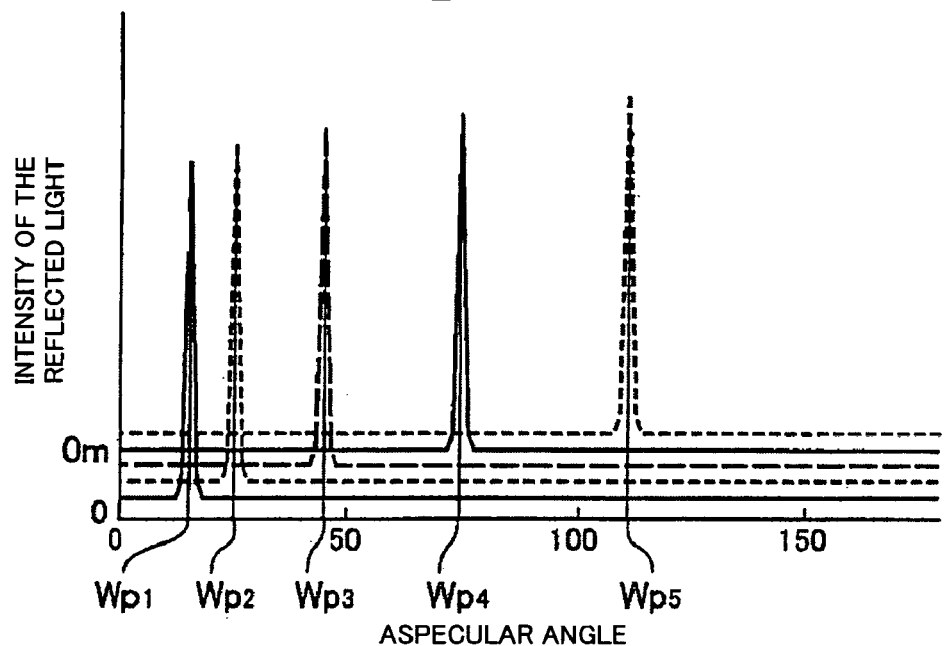
FIG. 24 is a graph showing the measured light intensity at varying aspecular angles using a jig 100.

FIG. 24 shows the relationship between the angle output Wi and the reflected light intensities Om (m=1 to 5) detected by the light receiving systems 20 to 60. The control PC 108 creates a data table as shown in FIG. 24 from the reflection light intensities Om detected every steps of rotation (step S208) and obtains an angle Wpm (m=1 to 5) where the output data Om (m=1 to 5) is highest for each of the five light receiving systems 20 to 60 (step S209) from the data. Then, based on the difference between the stored angle W0 for the specular reflection direction and the angle Wpm, the actual aspecular angle Bm' (=2·(Wpm−W0) (m=1 to 5)) is obtained (step S210). Subsequently thereto, the anormal angle $A_0$ (45 degrees) of the illumination direction is subtracted from the actual aspecular angle Bm' to obtain the actual anormal angle Am' (m=1 to 5) (step S211).

That is, the actual anormal angles Am' of the first to fifth light receiving systems 20 to 60 which are nominally −30, −20, 0, 30 and 65 degrees (denoted by Am) are calculated by the following equation (13):

$$Am'=Wpm-W0-A_0 \ (m=1 \text{ to } 5) \quad (13)$$

The differences between the actual anormal angles Am' and the nominal anormal angles Am are the initial angle errors of the first to fifth light receiving systems 20 to 60. The thus obtained actual anormal angles Am' (effectively same as initial angle errors) are stored in the memory 97 of the arithmetic control unit 90 and used for the error correction in the actual measurement. There can be an error also in the anormal angle $A_0$ (45 degrees) of the illumination system 10 and the influence thereof to the measured reflection characteristics. However, the reflection characteristic of the coating 110 containing the special effect flake pigments 111 is mainly affected by the error in the aspecular angle, and the influence of the error in the illumination direction is comparatively very small.

When measuring a sample surface 1 with the actual anormal angles Am' stored in the memory 97 as described above, the reflectance factors Rm (m=1 to 5) by the light receiving systems 20 to 60 are obtained and the approximation function I(A) correlating the measured reflectance factors Rm and the actual anormal angles Am' (m=1 to 5) is determined by the approximation function setter 94 similarly to the case of the above-described orientation error correction.

Then, the reflection characteristics error estimator 95 estimates the reflection characteristics error in each direction due to the angle error between the actual and the nominal anormal angle based on the approximation function I(A).

That is, the reflection characteristics error estimator 95 calculates the spectral reflectance factor I(Am) and I(Am') for the nominal anormal angle Am (m=1 to 5) and the actual anormal angle Am' respectively based on the approximation function I(A). Then, the reflection characteristics error estimator 95 calculates the difference therebetween as the estimated reflectance factor error ΔIm due to the initial angle error δm=Am'−Am by the following equation (14) (see FIG. 25):

$$\Delta Im = I(Am) - I(Am') \quad (14)$$

Then, the corrector 96 corrects the reflectance factor Rm (m=1 to 5) actually measured in each direction by use of the estimated error ΔIm based on the following equation (15):

$$Rm' = Rm + \Delta Im \quad (15)$$

Figure 25:
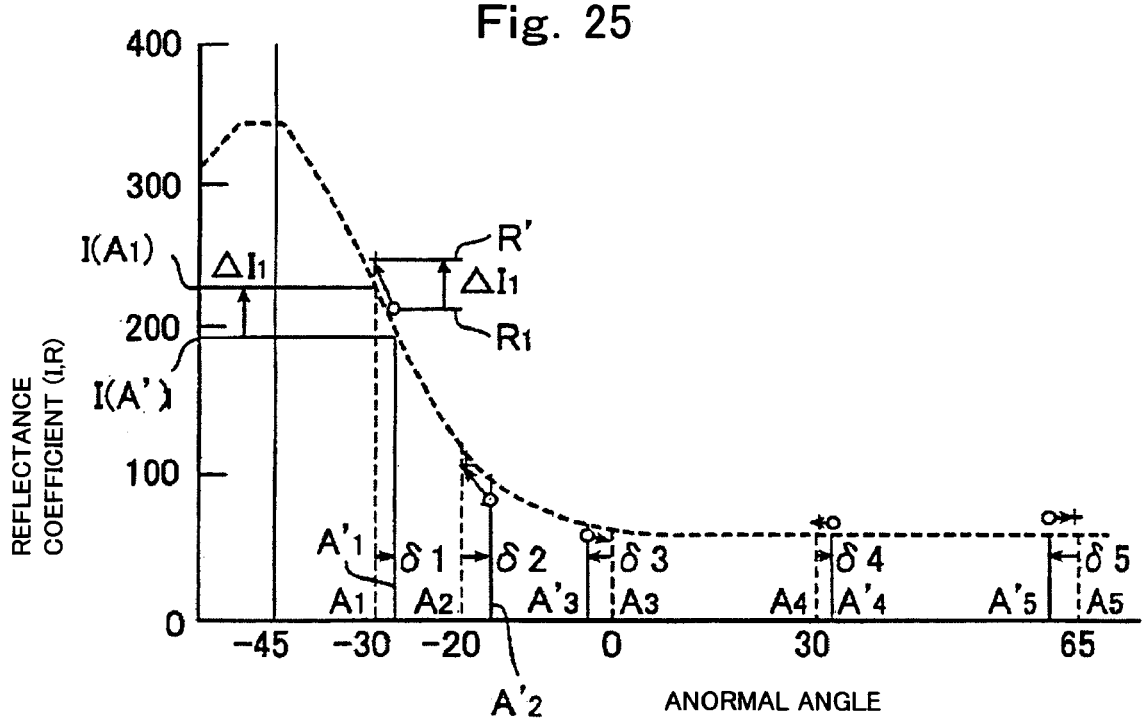
FIG. 25 is a graph for explaining the initial angle error correction by an approximation function.

While the orientation error δ is same for all light receiving directions in the above-described orientation error correction, in the case of the initial angle error correction, the angle errors in different directions generally differ from one another. This is because the initial angle errors are errors introduced individually to the first to fifth light receiving systems 20 to 60 when assembling. In the case of FIG. 25, for the nominal anormal angle A1 of −30 degrees, the actual anormal angles A1'>A1. Then, the measured reflectance factor R1 (o in FIG. 25) is corrected to R1' (+ in the figure) by the estimated reflectance factor error ΔI1=I(A1)−I(A1+δ1) with the use of equation, R1'=R1+ΔI1. Here, δ1 is the initial angle error obtained by the jig 100 and the flow of FIG. 23 for the nominal anormal angle A1 (−30 degrees).

While the initial angular error δ1 for the nominal anormal angle A1 is negative (leftward in FIG. 25), the initial angular error δ3 for the nominal anormal angle A3 (0 degrees) is positive (rightward in FIG. 25), since the actual aspecular angle A3'<A3.

For multi-angle colorimeters not having such a function, the initial angle error correction can also be performed using a jig similar to the above-described. In this case, all of the above-described process including those in measuring a sample surface is performed by an external PC or the like connected to the multi-angle colorimeter.

(Correction of All Geometry Errors)

The initial angular error and the orientation error described in the first embodiment can be corrected simultaneously because the corrections of those errors are based on a common technique as described above. However, the orientation error detector also includes an angular error and it is desirable to also correct this angular error. For the correction, a reference anormal angle Ac0 (deviation of the illumination system 70 with respect to the reference axis 2n) is previously obtained (step S203 of the flowchart shown in FIG. 23). The reference anormal angle Ac0 is obtained by measuring the anormal angle of the sample surface contacting the measurement aperture surface 2 correctly (with no orientation error) by the orientation error detector comprising the illumination system 70 and the first, third and fourth light receiving systems 30, 40 and 50.

The reference anormal angle Ac0, which is nominally 0 degree, is generally not 0 degree because of the geometry error of the illumination system 70. For the measurement of the reference anormal angle Ac0, a metallic reference surface such as silver metallic with the high reflectance factor is placed on the measurement aperture surface 2 in correct contact, and the actual anormal angle of the reference axis 2n is obtained by the method shown in FIGS. 21 and 22. That is, first, the illumination system 70 is turned on and the intensities Q1, Q3 and Q4 of the light reflected by the metallic reference surface are detected by the first, third and fourth light receiving systems 20, 40 and 50, (step S203). Then, the approximation function Z is obtained that correlates the reflectance factors not with the nominal anormal angles A1, A3 and A4 of the light receiving systems but with the previously obtained actual anormal angles A1', A3' and A4' (step S212). Then, the distribution center Ac0 of the obtained approximation function Z is stored into the memory 97 of the arithmetic control unit 90 as the reference anormal angle Ac0.

Figure 26:
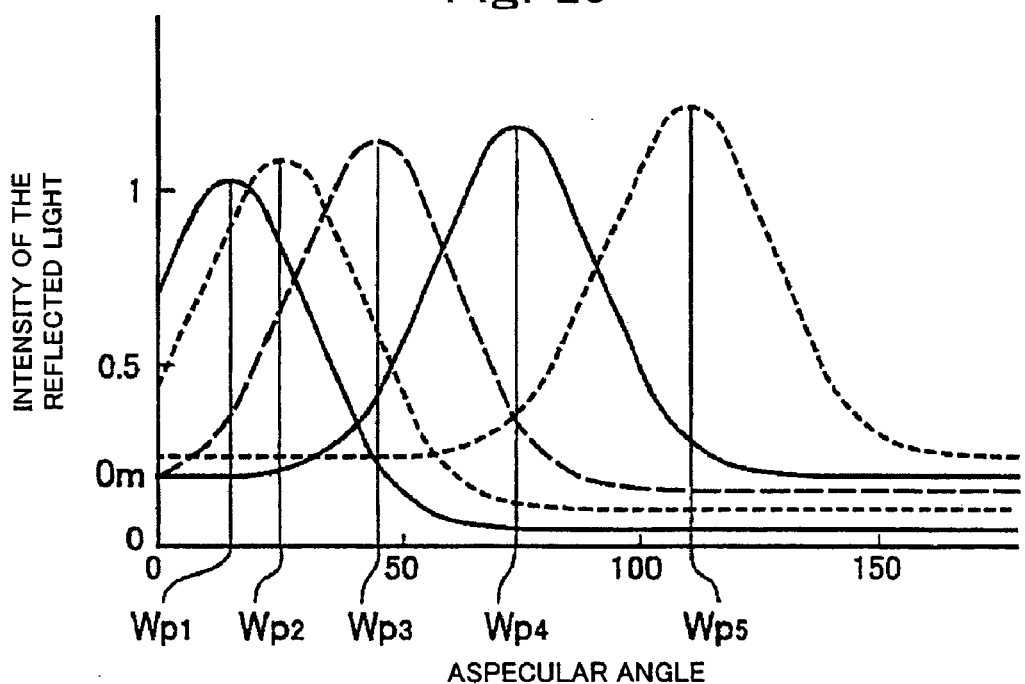
FIG. 26 is a graph showing the actual measured light intensity at varying aspecular angles using a jig 100 with a metallic coated plate as the reference reflecting surface.

The reference anormal angle Ac0 can be measured together with the actual anormal angles for the initial angular error correction by use of the same jig 100. In this case, since a black glass plate as the reference reflecting surface 101a reflects only specularly, the light emanated from the illumination system 70 and reflected thereby does not reach the first, third and fourth illumination systems 20, 40 and 50 within the measurement plane 2p. For receiving the reflected light by the receiving systems 20, 40 and 50, a metallic coated plate, for example, is disposed as the reference reflecting surface 101a. Then, the reference reflecting surface 101a is set in parallel to the reference surface 102, and the reference anormal angle Ac0 is obtained by a similar method as that of the orientation error correction. In the case of a jig using a metallic coated plate as the reference reflecting surface 101a, as shown in FIG. 26, the relation between the angle output W and the output data Om (m=1 to 5) of each light receiving system is like a Gaussian function and doesn't have as sharp peak as that of a black glass plate. For this reason, the center of Gaussian function approximating the relation is obtained and set as the actual aspecular angle of each light receiving system.

When measuring a sample surface by the multi-angle colorimeter S with the actual anormal angle Am' and the reference anormal angle Ac0 stored in the memory 97, a Gaussian function is obtained by the method described in FIG. 16 for the illumination of the illumination system 70, the distribution center Ac is obtained, and the orientation error δ is calculated by the following equation: δ=Ac−Ac0.

Then, the reflectance factors Rm (m=1 to 5) for the illumination of the illumination system 10 are measured by the light receiving systems 20 to 60 and an approximation function is obtained that correlates the measured reflectance factors Rm with the actual anormal angles Am' (m=1 to 5). The distribution center Ac is corrected by the orientation error δ obtained by the equation (4) shown above. The spectral reflectance factor I(Am+δ) for the nominal anormal angle Am+δ corrected for the orientation error and the reflectance factor I(Am') for the actual anormal angle Am' are calculated based on the approximation function, and the difference therebetween (ΔIm=I(Am+δ)−I(Am')) is obtained as the estimated reflectance factor error ΔIm due to all the geometry errors including the initial angle error and the orientation error. Then, by using the ΔIm, the actual measured reflectance factors Rm (m=1 to 5) are corrected by the following equation: Rm'=Rm+ΔIm.

Although the orientation error and the initial angle error are not dependent on the wavelength as mentioned above, since the reflection characteristic of the sample is dependent on the wavelength, the correction of the reflection characteristics by the orientation error and the initial angle error is performed specifically for each wavelength.

According to the above embodiment, the error of the reflection characteristics due to the orientation error and the initial angle error can be more accurately corrected. As a result, highly compatible colorimetric data can be obtained.

DESCRIPTION OF MODIFIED EMBODIMENTS

[A] The sensitivity of the reflection characteristics to the orientation error or the initial angle error is high in the vicinity of the specular reflection direction, and correction accuracy in this region is required as described based on FIG. 11. The correction amount for the reflectance factors in anormal angles of −30 degrees and −20 degrees calculated based on the approximation function which is obtained based on the measured reflectance factors in the five receiving directions including A1 (−30 degrees) and A2 (−20 degrees) of the first and second light receiving systems 20 and 30 and angular errors applied to the approximation function, has a sufficient accuracy between two directions. However, the accuracy of the outside is low. That is, since the anormal angles of −30 and −20 degrees are relatively close to each other, the approximation accuracy of the approximation function is high between these, however, for example, the anormal angle A3 (0 degrees) of the third light receiving system 40 is relatively far from the anormal angle A2 and the approximation accuracy between these is relatively low.

Figure 27:
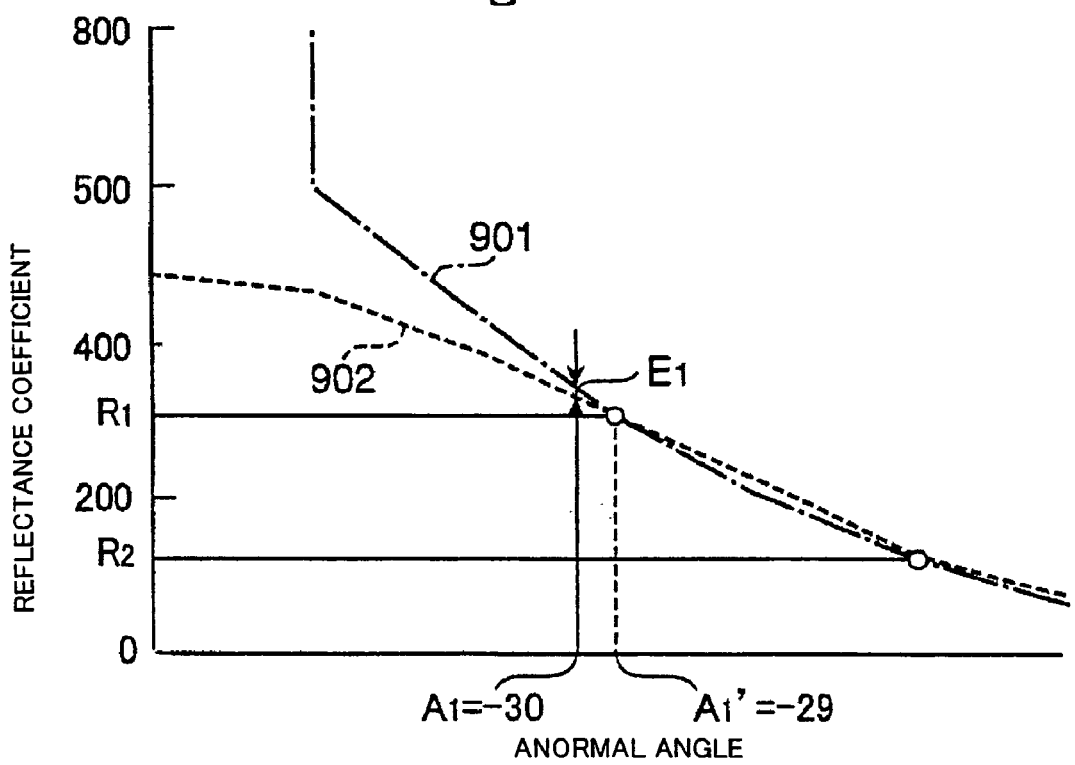
FIG. 27 is a graph showing the residual error of reflectance factors when the actual anormal angle A1' of a first light receiving system is −29 degrees and the nominal anormal angle A1 is −30 degrees.

In particular, as shown in FIG. 27, the accuracy is insufficient in the case that the actual anormal angle A1'=−29 and is larger than the nominal anormal angle A1=−30 degrees. In this case, it is necessary to make correction to the outside of the actual anormal angle A1' (left side of the figure). However, there is no measurement point outside the actual anormal angle A1' and this results large approximation error in the region. In the figure, the actually measured angular dependence of the reflectance factor 901 and the approximation function 902 differ more when the anormal angle A1 exceeds −30 degrees toward the minus (left) side due to the low approximation accuracy. This indicates that when correction is made toward the outside of the actual anormal angle A1' based on the approximation function, the residual error is possibly large like the case shown in FIG. 27 where the anormal angle A1' (−29 degrees) is corrected to the anormal angle A1 (−30 degrees) and results the residual error E1.

To improve this, assuming that all the geometry errors are within ±1 degrees, the anormal angle A1' is set to −31 degrees instead of −30 degrees. That is, the anormal angles of the five light receiving systems 20 to 60 are set to −31, −20, 0, 30 and 65 degrees, and the above-described correction is performed for this arrangement where the first light receiving system 20 closest to the specular reflection direction is intentionally displaced toward the specular reflection direction by a predetermined amount from the beginning.

In this case, the corrected reflectance factor in the direction of the anormal angle of −30 degrees is obtained by performing correction of the initial angle error for the nominal anormal angle of −30 degrees to the reflectance factor of the actual anormal angle of −31 degrees. That is, the actual anormal angle A1' is so preset that the correction is always made toward the inside (right side in the figure) of the actual anormal angle A1'. In FIG. 28, it is supposed that the actual anormal angle A1' is −32 degrees and the actual anormal angles A2' to A5' are equal to the nominal values, and −32 degrees is corrected to −30 degrees. The residual error E2 in this case is much smaller than the residual error E1 shown in FIG. 27 because the correction is performed between A1' and A2' where the approximation function 902 well approximates the actual angular dependence 901. According to this method, as far as the angle error is within ±1 degrees, the corrected angle stays inside the actual aspecular angles, and a high correction accuracy can be maintained. While it is assumed that there is no orientation error in this description, by setting the actual anormal angle A1' so that a correction for all the geometry errors including the orientation error is performed between anormal angles A1' and A2', a high correction accuracy can be maintained also for all the geometry errors.

[B] In the above-described embodiments, the orientation error detector is comprised of the illumination system 70 disposed within the measurement plane 2*q* and a plurality of light receiving systems disposed for multi-angle calorimetric measurements within the measurement plane 2*p*. However, the orientation error detector can be comprised of an illumination system and light receiving systems completely different from those for multi-angle calorimetric measurements.

[C] While in the above-described embodiments, an illumination system illuminates a sample from a single direction and a plural light receiving systems receives reflected light from the respective directions, the reverse geometry where illumination from a plural directions and light receiving from a single direction is also possible. In this case, the illumination system 10 and the illumination system 70 of FIGS. 2(*a*) and 2(*b*) are replaced with light receiving systems, and the first to fifth light receiving systems 20 to 60 are replaced with a first to fifth illumination systems, respectively. That is, either of the following embodiments can be adopted: an embodiment in which a sample surface 1 is illuminated from a single specific direction and the reflected light therefrom is received from plural directions; and a embodiment in which a sample surface 1 is illuminated from plural directions and the reflected light therefrom is received from a single specific direction.

According to the above-described embodiment, the angle errors such as the initial angle error and the orientation error are detected by an angle error detector or a jig comprising an illuminator and a light receiving system different from those for calorimetric measurement. Consequently, (1) The illumination system for an orientation error can be set in the direction different from the illumination system for calorimetric measurement at 45 degrees of anormal angle. This arrangement results higher accuracy than when illuminating from 45 degrees of anormal angle. The orientation error is obtained by performing approximation of the directional dependence of the reflection characteristics by mathematical function like the conventional method but with higher accuracy. (2) Detection of the initial angular error is virtually impossible by measurement system comprising the illuminator and the light receivers in the multi-angle colorimeter. However, by providing a reference reflecting surface capable of varying the reflection direction (reflection angle) of light from the illuminator, that is, by providing a different measurement system including the reference reflecting surface from that for calorimetric measurement, the data for the initial angle error detection can be obtained.

Although the present invention has been fully described by way of examples with reference to the accompanying drawings, it is to be noted that various change and modifications will be apparent to those skilled in the art. Therefore, unless otherwise such changes and modifications depart from the scope of the present invention, they should be construed as being including therein.

What is claimed is:

1. A multi-angle colorimeter comprising:
    one or plural illuminators for illuminating a surface of an object to be measured from one or plural directions and for measuring a colorimetric value of the surface of the object;
    one or plural light receivers for receiving reflected light from the surface illuminated by said one or plural illuminators respectively, and for measuring a colorimetric value of the surface of the object;
    a reflection characteristics calculator for calculating a reflectance characteristics of the surface for plural directions of illumination or light receiving;
    an angular error detector for detecting an angular error of the illuminators and the light receivers with respect to the surface, and comprising a measurement system different from the illuminators and the light receivers;
    an approximation function setter for determining an approximation function that approximates a directional dependence of the reflectance characteristics of the surface based on the detected angular error and the reflection characteristics obtained by said reflection characteristics calculator;
    a reflection characteristics error estimator for estimating an error of the reflection characteristics in each measurement direction based on the determined approximation function and the detected angular error; and
    a corrector for correcting the obtained reflection characteristics in each measurement direction based on the estimated reflection characteristics error.

2. The multi-angle colorimeter according to claim 1, wherein the angular error detector detects an orientation error of the illuminators and the light receivers with respect to the surface of the object.

3. The multi-angle colorimeter according to claim 2, wherein the angular error detector comprises illuminators and light receivers for orientation error detection.

4. The multi-angle colorimeter according to claim 3,
    wherein the illuminators for orientation error detection illuminate the surface of the object from at least one direction,
    wherein the light receivers for orientation error detection receive reflected light from the surface illuminated in at least one direction, and
    wherein the angular error detector obtains an approximation function approximating a relationship between anormal angles and the reflected light intensities, and detects an orientation error of the illuminators for colorimetric measurement and light receivers for colorimetric measurement with respect to the surface of the object based on the anormal angle of a central axis of the approximation function.

5. The multi-angle colorimeter according to claim 4,
    wherein the illuminator for orientation error detection illuminates the surface of the object from a direction substantially close to the normal of the surface, and
    wherein the light receivers for orientation error detection receive the reflected light from the surface illuminated in the plurality of directions with the normal of the surface as the center.

6. The multi-angle colorimeter according to claim 4,
    wherein the illuminators for orientation error detection illuminate the surface of the object from a plurality of directions with the normal of the surface as the center, and
    wherein the light receiver for orientation error detection receives the reflected light from the surface illuminated in a direction substantially close to the normal of the surface.

7. The multi-angle colorimeter according to claim 3,
    wherein the illuminators for colorimetric measurement and the light receivers for colorimetric measurement are disposed in a first measurement plane containing a reference axis of the multi-angle colorimeter, wherein the illuminators for orientation error detection and the light receivers for orientation error detection are disposed in a second measurement plane containing the reference axis of the multi-angle colorimeter and orthogonal to the first measurement plane, and wherein at least one of the illuminators for colorimetric measurement or the light receivers for colorimetric measurement is used as the illuminator for orientation error detection or light receiver for orientation error detection, respectively.

8. The multi-angle colorimeter according to claim 1, wherein the angular error detector detects initial angular errors of the illuminators for colorimetric measurement and the light receivers for colorimetric measurement with respect to a normal of the surface of the object.

9. The multi-angle colorimeter according to claim 8, wherein the angular error detector comprises a reference reflecting member having a reference reflecting surface, and a positioning member of the reference reflecting member enabling the light emanated from the illuminator for colorimetric measurement and reflected by the reference reflecting surface to be incident on the light receivers for colorimetric measurement.

10. The multi-angle colorimeter according to claim 9, wherein the angular error detector detects a deviations of actual aspecular angles of the illuminators for colorimetric measurement or the light receivers for colorimetric measurement from nominal aspecular angles thereof, by comparing nominal aspecular angles and actual aspecular angles obtained by use of the reference reflecting member, wherein the approximation function setter determines approximation function approximating the directional dependence of the reflection characteristics of the surface by use of the actual aspecular angles, wherein the reflection characteristics error estimator estimates the reflection characteristics error in each direction based on the approximation function, the actual aspecular angle and the nominal aspecular angle, and wherein the corrector corrects the reflection characteristics in each direction of the actual aspecular angle to that of the nominal aspecular angle by the use of the estimated reflection characteristics error in each direction.

11. The multi-angle colorimeter according to claim 1, wherein, the closest one to the specular reflection direction among plural illuminators for colorimetric measurement is placed at shifted position by a predetermined small angle from the nominal angle toward the specular reflection direction.

12. The multi-angle colorimeter according to claim 1, wherein, the closest one to the specular reflection direction among plural light receivers for colorimetric measurement is placed at shifted position by a predetermined small angle from the nominal angle toward the specular reflection direction.

13. The multi-angle colorimeter according to claim 1, wherein the object to be measured is a coating containing special effect flake pigments.

14. The multi-angle colorimeter according to claim 13, wherein the approximation function approximating the directional dependence of the reflectance characteristics of the surface comprises a Gaussian function expressing the angular distribution of the special effect flake pigments within the coating combined with at least one of the following supplemental functions (a) to (d):

(a) a function based on Snell's law representing refraction of light at boundary of the coating and the air;

(b) a function based on Lambert's law representing the direction dependence of the reflected light by a perfect reflecting diffuser used as a reference of a reflectance factor;

(c) a function based on Fresnel reflection law representing reflection of light at boundary of the coating and the air; and (d) a function representing an effective cross-sectional area of the special effect flake pigments contributing to specific combination of illumination and light receiving directions.

15. A method of measuring characteristics of a material containing special effect flake pigments using a multi-angle colorimeter, comprising the steps of:

illuminating a surface of an object to be measured from one or plural directions by at least one of illuminator;

receiving reflected light from the surface illuminated in one or plural directions by at least one of light receiver;

calculating reflectance characteristics of the surface in plural directions;

detecting an angular error of the illuminator and the light receiver with respect to the surface by a measurement system different from the illuminator and the light receiver;

determining an approximation function that approximates a directional dependence of the reflectance characteristics based on the detected angular error and the calculated reflection characteristics;

estimating an error of the reflection characteristics in each measurement direction based on the determined approximation function and the detected angular error;

correcting the calculated reflection characteristic in each measurement direction based on the estimated error of the reflection characteristic; and, outputting said corrected reflection characteristic in each measurement direction.

* * * * *